US009510790B2

(12) United States Patent
Kang et al.

(10) Patent No.: US 9,510,790 B2
(45) Date of Patent: Dec. 6, 2016

(54) METHOD FOR MEASURING BIOLOGICAL SIGNAL AND WEARABLE ELECTRONIC DEVICE FOR THE SAME

(71) Applicant: Samsung Electronics Co., Ltd., Gyeonggi-do (KR)

(72) Inventors: Jeong-Gwan Kang, Gyeonggi-do (KR); Byung-Jun Lee, Gyeonggi-do (KR); Hyun-Su Hong, Gyeonggi-do (KR); Seung-Hyuck Shin, Gyeonggi-do (KR); Sun-Young Park, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/974,708

(22) Filed: Dec. 18, 2015

(65) Prior Publication Data
US 2016/0249864 A1    Sep. 1, 2016

(30) Foreign Application Priority Data
Feb. 27, 2015   (KR) .......................... 10-2015-0028418

(51) Int. Cl.
*G08C 19/22* (2006.01)
*A61B 5/00* (2006.01)
*A61B 5/024* (2006.01)

(52) U.S. Cl.
CPC ........... *A61B 5/7285* (2013.01); *A61B 5/0002* (2013.01); *A61B 5/02438* (2013.01); *A61B 5/681* (2013.01)

(58) Field of Classification Search
None
See application file for complete search history.

(56) References Cited

U.S. PATENT DOCUMENTS

| 6,287,262 B1 | 9/2001 | Amano et al. |
|---|---|---|
| 2010/0113948 A1 | 5/2010 | Yang et al. |
| 2011/0152637 A1 | 6/2011 | Kateraas et al. |
| 2012/0165684 A1 | 6/2012 | Sholder |
| 2012/0316455 A1* | 12/2012 | Rahman ............... G01C 22/006 600/547 |
| 2012/0316456 A1* | 12/2012 | Rahman ................. G06F 1/163 600/547 |

(Continued)

FOREIGN PATENT DOCUMENTS

| JP | 2007-195699 A | 8/2007 |
|---|---|---|
| JP | 2012-235920 A | 12/2012 |
| WO | 2010/108287 A1 | 9/2010 |

OTHER PUBLICATIONS

European Search Report dated Jul. 29, 2016.

*Primary Examiner* — Ojiako Nwugo
(74) *Attorney, Agent, or Firm* — Cha & Reiter, LLC

(57) ABSTRACT

According to an embodiment of the present disclosure, there is a wearable electronic device, comprising: a first sensor configured to sense a movement of the electronic device; a second sensor configured to sense a biological signal for a user wearing the electronic device; and a processor configured to compute a movement value of the electronic device using the first sensor, to detect a resting state when the movement value lasts within a predetermined first threshold range during a first time period, and to configure biological information of the user based on a biological signal measured after detection of the resting state.

24 Claims, 16 Drawing Sheets

(56) References Cited

U.S. PATENT DOCUMENTS

2013/0173171 A1* 7/2013 Drysdale ............... A61B 5/1118
                                                       702/19
2014/0128752 A1   5/2014 Donaldson
2014/0275854 A1   9/2014 Venkatraman et al.
2014/0278220 A1   9/2014 Yuen

* cited by examiner

METHOD FOR MEASURING BIOLOGICAL SIGNAL AND WEARABLE ELECTRONIC DEVICE FOR THE SAME

CLAIM OF PRIORITY

This application claims the benefit under 35 U.S.C. §119(a) of a Korean patent application filed in the Korean Intellectual Property Office on Feb. 27, 2015 and assigned Serial No. 10-2015-0028418, the entire disclosure of which is incorporated herein by reference.

TECHNICAL FIELD

The present disclosure relates to wearable electronic devices for measuring biological signals.

DISCUSSION OF RELATED ART

Electronic devices may carry out various functions in an integrated manner. For example, smartphones or other portable terminals are advancing to allow users more convenience with better performance. Wearable electronic devices recently developed are a sort of electronic devices with shapes such as wristwatches, headsets, or glasses that may be put on user's body. As such, electronic devices nowadays go beyond their own unique functionalities and converge with other portable devices.

More attention is directed to health and leads to vigorous research efforts in electronic device-based healthcare applications. Sensors of an electronic device may gather information relating to the electronic device, the exterior of the electronic device, or information regarding the user. Among others, steady measurement of biological signals is critical in a check-up on the user's physical condition. The demand for technology that may monitor the user's condition during a workout or diet session is prompting the development of electronic devices equipped with the functionality of checking the user's heart rate.

A normal resting heart rate refers to a beat count per minute measured while the user lies on the bed. Taking an average of values measured during the same time duration consecutively five or more days as a resting heart rate reduces errors in measurement. However, it is tough for the user to measure their heart rate in the same time duration right before they get up. Five to ten minutes of relaxation prior to measurement of the heart rate using the electronic device also results in a more accurate measurement. Further, this can be quite inconvenient for many users.

Consecutively check the user's heart rate 24 hours using an electronic device to address such issues results in significant battery consumption. The foregoing also fails to distinguish the user's resting heart rate from those measured for the period. Accordingly, the foregoing is not a suitable idea for portable electronic devices.

The above information is presented as background information only to assist with an understanding of the present disclosure. No determination has been made, and no assertion is made, as to whether any of the above might be applicable as prior art with regard to the present disclosure.

SUMMARY

According to an embodiment of the present disclosure, there are provided a method for automatically measuring a user's biological signal depending on the user's condition in a wearable electronic device and a wearable electronic device for the same. According to an embodiment of the present disclosure, there are a method for detecting a user's resting state to measure a biological signal corresponding to the resting state without the need of remaining still for the measurement and a wearable electronic device for the same.

According to an embodiment of the present disclosure, there is a method for reducing power consumption by activating a sensor for measuring a biological signal when the user is determined to be in a resting state based on the detection of a movement of an electronic device put on the user and a wearable electronic device for the same.

According to an embodiment of the present disclosure, there is a wearable electronic device, comprising: a first sensor configured to sense a movement of the electronic device; a second sensor configured to sense a biological signal for a user wearing the electronic device; and a processor configured to compute a movement value of the electronic device using the first sensor, to detect a resting state when the movement value lasts within a predetermined first threshold range during a first time period, and to configure biological information of the user based on a biological signal measured after detection of the resting state.

According to an embodiment of the present disclosure, a method for measuring biological information using a wearable electronic device, comprises: sensing a movement of the electronic device; computing a movement value of the electronic device using the sensed movement and detecting a resting state when the movement value is within a predetermined first threshold range during a first time period; and configuring biological information of a user wearing the electronic device based on a biological signal for the user measured after detection of the resting state.

Other aspects, advantages, and salient features of the disclosure will become apparent to those skilled in the art from the following detailed description, which, taken in conjunction with the annexed drawings, discloses exemplary embodiments of the disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

Throughout the drawings, like reference numerals will be understood to refer to like parts, components, and structures.

DETAILED DESCRIPTION

Figure 1:
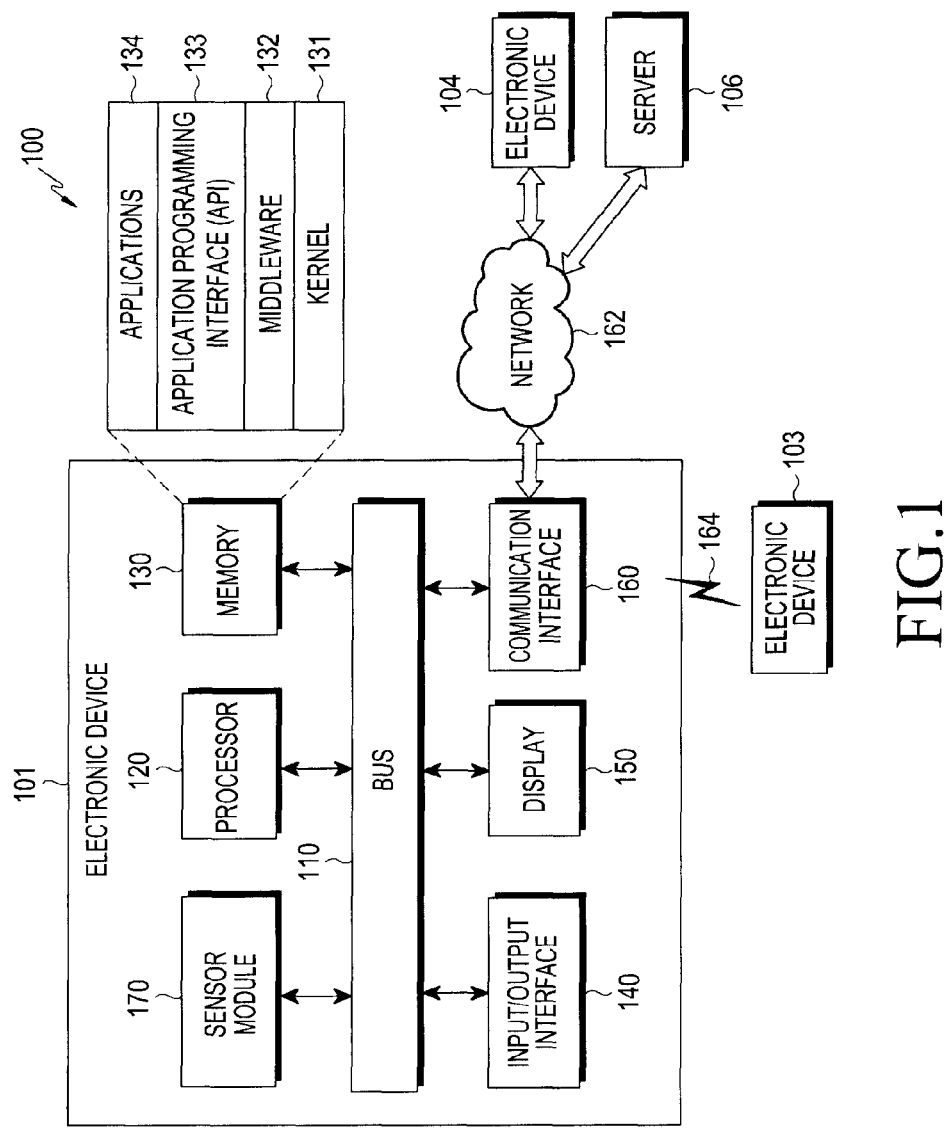
FIG. 1 is a view illustrating a network environment including an electronic device according to an embodiment of the present disclosure.

Hereinafter, embodiments of the present disclosure are described with reference to the accompanying drawings. However, it should be appreciated that the present disclosure is not limited to the embodiments, and all changes and/or equivalents or replacements thereto also belong to the scope of the present disclosure. The same or similar reference denotations may be used to refer to the same or similar elements throughout the specification and the drawings.

As used herein, the terms "have," "may have," "include," or "may include" a feature (e.g., a number, function, operation, or a component such as a part) indicate the existence of the feature and do not exclude the existence of other features.

As used herein, the terms "A or B," "at least one of A and/or B," or "one or more of A and/or B" may include all possible combinations of A and B. For example, "A or B," "at least one of A and B," "at least one of A or B" may indicate all of (1) including at least one A, (2) including at least one B, or (3) including at least one A and at least one B.

As used herein, the terms "first" and "second" may modify various components regardless of importance and/or order and are used to distinguish a component from another without limiting the components. For example, a first user device and a second user device may indicate different user devices from each other regardless of the order or importance of the devices. For example, a first component may be denoted a second component, and vice versa without departing from the scope of the present disclosure.

It will be understood that when an element (e.g., a first element) is referred to as being (operatively or communicatively) "coupled with/to," or "connected with/to" another element (e.g., a second element), it can be coupled or connected with/to the other element directly or via a third element. In contrast, it will be understood that when an element (e.g., a first element) is referred to as being "directly coupled with/to" or "directly connected with/to" another element (e.g., a second element), no other element (e.g., a third element) intervenes between the element and the other element.

As used herein, the terms "configured (or set) to" may be interchangeably used with the terms "suitable for," "having the capacity to," "designed to," "adapted to," "made to," or "capable of" depending on circumstances. The term "configured (or set) to" does not essentially mean "specifically designed in hardware to." Rather, the term "configured to" may mean that a device can perform an operation together with another device or parts. For example, the term "processor configured (or set) to perform A, B, and C" may mean a generic-purpose processor (e.g., a CPU or application processor) that may perform the operations by executing one or more software programs stored in a memory device or a dedicated processor (e.g., an embedded processor) for performing the operations.

The terms as used herein are provided merely to describe some embodiments thereof, but not to limit the scope of other embodiments of the present disclosure. It is to be understood that the singular forms "a," "an," and "the" include plural references unless the context clearly dictates otherwise. The terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the present disclosure.

For example, examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a PDA (personal digital assistant), a portable multimedia player (PMP), an MP3 player, a mobile medical device, a camera, or a wearable device. According to an embodiment of the present disclosure, the wearable device may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device (e.g., an implantable circuit).

According to an embodiment of the present disclosure, the electronic device may be a home appliance. For example, examples of the home appliance may include at least one of a television, a digital video disk (DVD) player, an audio player, a refrigerator, an air conditioner, a cleaner, an oven, a microwave oven, a washer, a drier, an air cleaner, a set-top box, a home automation control panel, a security control panel, a TV box (e.g., Samsung HomeSync™, Apple TV™, or Google TV™), a gaming console (Xbox™, PlayStation™), an electronic dictionary, an electronic key, a camcorder, or an electronic picture frame.

According to an embodiment of the present disclosure, examples of the electronic device may include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global navigation satellite system (GNSS) receiver, an event data recorder (EDR), a flight data recorder (FDR), an automotive infotainment device, an sailing electronic device (e.g., a sailing navigation device or a gyro compass), avionics, security devices, vehicular head units, industrial or home robots, automatic teller's machines (ATMs), point of sales (POS) devices, or Internet of Things devices (e.g., a bulb, various sensors, an electric or gas meter, a sprinkler, a fire alarm, a thermostat, a street light, a toaster, fitness equipment, a hot water tank, a heater, or a boiler).

According to various embodiments of the disclosure, examples of the electronic device may at least one of part of furniture or building/structure, an electronic board, an electronic signature receiving device, a projector, or various measurement devices (e.g., devices for measuring water, electricity, gas, or electromagnetic waves). According to an embodiment of the present disclosure, the electronic device may be one or a combination of the above-listed devices. According to an embodiment of the present disclosure, the electronic device may be a flexible electronic device. The electronic device disclosed herein is not limited to the above-listed devices, and may include new electronic devices depending on the development of technology.

Hereinafter, electronic devices are described with reference to the accompanying drawings, according to various embodiments of the present disclosure. As used herein, the term "user" may denote a human or another device (e.g., an artificial intelligent electronic device) using the electronic device.

FIG. 1 illustrates a network environment 100 including an electronic device 101 according to an embodiment of the present disclosure. Referring to FIG. 1, the electronic device 101 may be a device that may be worn on a portion of the user's body, such as their wrist, arm, head, ankle, or face, and the external electronic devices 103 and 104 may be portable devices that may communicate with the electronic device 101.

Referring to FIG. 1, the electronic device 101 may include a bus 110, a processor 120, a memory 130, an input/output interface 140, a display 150, a communication interface 160, and a sensor module 170. In some embodiments, the electronic device 101 may exclude at least one of the components or may add another component.

The bus 110 may include a circuit for connecting the components 120 to 170 with one another and transferring communications (e.g., control messages and/or data) between the components.

The processing module 120 may include one or more of a central processing unit (CPU), an application processor (AP), or a communication processor (CP). The processor 120 may perform control on at least one of the other components of the electronic device 101, and/or perform an operation or data processing relating to communication. The processor 120 may receive a command from other component (e.g., the memory 130, the input/output interface 140, the display 150, the communication interface 160, or the sensor module 170) through, e.g., the bus 110, may interpret the received command, and may execute computation or data processing according to the interpreted command.

The processor 120 may be denoted a controller, or the processor 120 may include a controller as part thereof.

According to an embodiment of the present disclosure, the processor 120 may perform the operation of sensing a movement of the electronic device 101 (for example, in conjunction with the sensor module 170), the operation of computing a movement value of the electronic device using the sensed movement to determine a resting time when the movement value is maintained within a predetermined first threshold range during a first time interval, and the operation of configuring bio information of a user wearing the electronic device based on a biological signal for the user measured after the resting time.

Specifically, the processor 120 may determine whether the electronic device 101 is worn based on data sensed from the sensor module 170, and when the electronic device 101 is worn, may compute movement strengths of the electronic device 101 to determine a variation in movement strength and to determine whether the variation in movement strength is maintained for a predetermined time within a predetermined threshold range. When the variation in movement strength is maintained for the predetermined time within the predetermined threshold range is considered to be in a resting state where there is little or no movement of the user, and a bio sensor for measuring a biological signal may be activated to measure a biological signal in the resting state.

According to an embodiment of the present disclosure, the processor 120 may activate at least one bio sensor included in the sensor module 170, and the bio sensor may accordingly measure various biological signals from the user's body to output various bio sensor values related to the user's body. According to an embodiment of the present disclosure, among the bio sensors, a heart rate sensor may be activated to measure a heart rate. Besides, other biological signals, such as the user's blood pressure, blood flow, respiration rate, oxygen saturation, cardiorespiratory sound, or blood sugar, may be measured to determine the user's state in the resting state.

As described above, at the time of being determined to be in the resting state based on the detection of a movement of the electronic device 101 put on the user, the bio sensor may be activated to measure a heart rate. Thus, power consumption of the electronic device 101 may be minimized. According to an embodiment of the present disclosure, since the bio sensor is activated considering a previous movement state even when it is determined to be in the resting state, a more accurate result of measurement of a heart rate corresponding to the resting state may be obtained.

The memory 130 may store a command or data received from other component (e.g., the input/output interface 140, the display 150, the communication interface 160, or the sensor module 170) or a command or data generated by the processor 120 or other component. The memory 130 may retain programming modules including, e.g., a kernel 131, middleware 132, an application programming interface (API) 133, or an application 134. The programming modules may comprise a portion of memory storing a plurality of machine-readable instructions.

The memory 130 may store sensing data measured by one or more sensors included in the sensor module 170. The memory 130 may further store sensing data (e.g., speed, acceleration, or traveling direction of the electronic device 101) measured by an acceleration sensor or gyro sensor included in the sensor module 170. The memory 130 may further store sensor values to analyze the speed, acceleration, or traveling direction of the electronic device 101 to determine the user's current moving state or movement (e.g., walking, jogging, or sleeping).

The memory 130 may previously retain data to determine whether the electronic device 101 is worn based on the sensing data. Further, the memory 130 may previously retain data to determine a state where the user comes to rest and is in a stable condition while the user does their daily routine with the electronic device 101 on them. Further, bio sensor values measured in every resting state where the variation in movement strength is maintained for a predetermined time within a predetermined threshold range may be recorded in the memory 130. According to an embodiment of the present disclosure, biological signals, such as heart rates, body temperatures, or skin resistances, may be measured whenever the resting state comes up. Further, upon storing a bio sensor value, information collected under the control of the processor 120 may be stored as well. For example, the place corresponding to the location information on the electronic device 101, time of the measurement, or use history of the application on the electronic device 101 may be stored, mapped with bio information configured based on the bio sensor values.

The kernel 131 may control or manage system resources (e.g., the bus 110, the processor 120, or the memory 130) used to execute the operation or function implemented in the other programming modules, e.g., the middleware 132, the API 133 or the application 134. The kernel 131 may provide an interface that allows the middleware 132, the API 133, or the application 134 to access the individual components of the electronic device 101 to control or manage the same.

The middleware 132 may function as a relay to allow the API 133 or the application 134 to communicate data with the kernel 131. A plurality of applications 134 may be provided. The middleware 132 may perform control in response to work requests received from the applications 134, e.g., by allocating the priority of using the system resources of the electronic device 101 (e.g., the bus 110, the processor 120, or the memory 130) to at least one of the plurality of applications 134 in relation to the work requests.

The API 133 is an interface allowing the application 134 to control functions provided from the kernel 131 or the middleware 132. For example, the API 133 may include at least one interface or function (e.g., a command) for filing control, window control, image processing or text control.

According to an embodiment of the present disclosure, there may be provided a plurality of applications 134 including a short message service (SMS)/multimedia messaging service (MMS) application, an email application, a calendar application, an alarm application, a health care application (e.g., an application for monitoring a state of measuring a heart rate or an application for measuring calorie consumption based on the heart rate), or an environmental information application (e.g., an application providing atmospheric pressure, moisture, or temperature information). Further, the application 134 may be an application related to information exchange between the electronic device 101 and an external electronic device (e.g., electronic device 103 or 104). Examples of the information exchange-related application may include, but is not limited to, a notification relay application for transferring specific information to the external electronic device, or a device management application for managing the external electronic device.

For example, in the case of the health care application, the user may execute the health care application to access the health care server 106 or external electronic device 104. Here, the electronic device 101 may receive location information from the electronic device 103 via the communication interface 160.

The user may measure bio information using a bio sensor included in the sensor module 170. The electronic device 101 may transmit a measurement value of bio information to the external electronic device 104 or healthcare server 106 via the communication interface 160. In case the electronic device 101 transmits the measurement value to the healthcare server 106, the electronic device 101 may obtain a diagnosis result for the measurement value from the healthcare server 106 and may display the diagnosis result on the display 150 or provide the same to the user through, e.g., an alert sound or voice message. According to an embodiment of the present disclosure, the electronic device 101 may transmit the measurement value of the bio information to the healthcare server 106 or the external electronic device 104 and may output information corresponding to the measurement value of the bio information.

Here, the external electronic device 104 may receive the measurement value of the bio information from the electronic device 101, collect, generate, manage, store, provide, or process the information, and may send a result back to the electronic device 101. To that end, the external electronic device 104 may be implemented to be similar in configuration to the electronic device 101.

According to an embodiment of the present disclosure, the applications 134 may include an application designated according to an attribute (e.g., type of the electronic device) of the external electronic device (e.g., the electronic device 104). Further, the applications 134 may include at least one of an application designated to the electronic device 101 or an application received from an external electronic device (e.g., the health care server 106 or the electronic device 104).

The input/output interface 140 may transfer commands or data input by the user through an input/output device (e.g., a keyboard or touch screen) to the processor 120, the memory 130, or the communication interface 160 through, e.g., the bus 110. For example, the input/output interface 140 may provide data for an input means, such as the user's finger or an electronic pen, input through the touch screen, to the processor 120.

According to an embodiment of the present disclosure, the input unit of the input/output interface 140 may include a touch panel, a (digital) pen sensor, a key, or an ultrasonic input device. The touch panel may recognize touch inputs in at least one of capacitive, resistive, infrared, or ultrasonic methods. The touch panel may be implemented as at least one or more panels that may sense various inputs, such as the user's single or multi-touch input, a drag input, a handwriting input, or a drawing input, using various objects, such as a finger or pen.

For example, the touch panel may be implemented using a single panel that may sense both a finger input and a pen input or using two panels including a touch recognition module that may sense a finger input and a pen recognition module that may sense a pen input. Further, the touch panel may further include a control circuit. With the capacitive method, physical contact or proximity detection may be possible. The touch panel may further include a tactile layer.

In this regard, the touch panel may provide the user with a tactile response. The input/output interface 140 may output, through the input/output device (e.g., a speaker or display), commands or data received from the processor 120, the memory 130, the communication interface 160, or the sensor module 170 through, e.g., the bus 110.

The display 150 may display various types of information (e.g., multimedia data or text data) to the user. According to an embodiment of the present disclosure, the display 150 may display a screen for identifying a bio information measurement result for the user. The display 150 may be implemented as a touch screen. The touch screen may be provided with a display panel performing a display function for information output from the electronic device 101 and an input panel performing various input functions by the user. The display panel may be a panel, such as, e.g., a liquid crystal display (LCD) or active-matrix organic light emitting diode (AMOLED) panel.

The display panel may display various screens according to various operation states of the electronic device 101, application execution, and services.

The input panel may be implemented as at least one or more panels that may sense various inputs, such as the user's single or multi-touch input, a drag input, a handwriting input, or a drawing input, using various objects, such as a finger or pen. For example, the input panel may be implemented using a single panel that may sense both a finger input and a pen input or using two panels including a touch recognition module that may sense a finger input and a pen recognition module that may sense a pen input.

Such touch screen may output, to a touch screen controller, a signal corresponding to at least one user input to the user graphic interface. The touch screen may receive at least one user input through the user's body (e.g., an index finger or other finger). The touch screen may receive a continuous motion of a touch. The touch screen may output an analog signal corresponding to the continuous motion of the input touch to the touch screen controller.

According to an embodiment of the present disclosure, the touch is not limited to a contact between the touch screen and a user input means, such as a finger, and rather may include a non-contact (for example, the case where the user input means is positioned within a recognition distance (e.g., 1 cm) where the user input means may be detected without a direct contact with the touch screen). The distance or interval within which the user input means may be recognized on the touch screen may be varied depending on the performance or structure of the electronic device 101. In particular, the touch screen may be configured to output a value detected by a direct touch event (by a contact of the user input means to the touch screen) and a value (including, e.g., a voltage value or current value as an analog value) detected by an indirect touch event (i.e., a hovering event), which are different from each other, so that the direct touch event and the hovering event may be detected distinct from each other.

Such touch screen may be implemented, e.g., in a capacitive, infrared, or acoustic wave manner, or in a combination thereof.

The touch screen controller converts a signal input from the touch screen into a digital signal and transmits the same to the controller. The controller may control the user interface displayed on the touch screen using the digital signal received from the touch screen controller. For example, the controller may allow a shortcut icon (not shown) displayed on the touch screen or object to be selected or executed in response to the direct touch event or hovering event. Further, the touch screen controller may be integrated with the controller.

The touch screen controller may identify a hovering interval or distance as well as the position of the user's input by detecting the value (e.g., a current value) output through the touch screen and may convert the identified distance value into a digital signal (e.g., a Z axis) and provide the same to the controller.

The communication interface 160 may establish communication between the electronic device 101 and an external electronic device (e.g., the electronic device 104 or the health care server 106). For example, the communication interface 160 may be connected with the network 162 through wireless or wired communication to communicate with the external device (e.g., the external electronic device 104 or the healthcare server 106).

The wireless communication may be a cellular communication protocol and may use at least one of, e.g., long-term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM). Further, the wireless communication may include, e.g., short-range communication 164. The short-range communication 164 may include at least one of wireless fidelity (Wi-Fi), Bluetooth, near-field communication (NFC), or global navigation satellite system (GNSS). The GNSS may include at least one of, e.g., global positioning system (GPS), global navigation satellite system (Glonass), Beidou navigation satellite system (hereinafter, "Beidou") or Galileo, or the European global satellite-based navigation system. Hereinafter, the terms "GPS" and the "GNSS" may be interchangeably used herein. The wired connection may include at least one of, e.g., universal serial bus (USB), high definition multimedia interface (HDMI), recommended standard (RS)-232, or plain old telephone service (POTS). The network 162 may include at least one of telecommunication networks, e.g., a computer network (e.g., LAN or WAN), Internet, or a telephone network.

The external electronic devices 103 and 104 each may be a device of the same or a different type from the electronic device 101. According to an embodiment of the present disclosure, the healthcare server 106 may include a group of one or more servers. According to an embodiment of the present disclosure, all or some of operations executed on the electronic device 101 may be executed on another or multiple other electronic devices (e.g., the external electronic devices 103 and 104 or healthcare server 106). According to an embodiment of the present disclosure, when the electronic device 101 should perform some function or service automatically or at a request, the electronic device 101, instead of executing the function or service on its own or additionally, may request another device (e.g., electronic devices 103 and 104 or healthcare server 106) to perform at least some functions associated therewith. The other electronic device (e.g., electronic devices 103 and 104 or healthcare server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

According to an embodiment of the present disclosure, the electronic device 101 may be connected with the healthcare server 106 through the network 162. The electronic device 101 may transmit a result of bio information measurement to the healthcare server 106 and obtain health-related information created based on the result of the bio information measurement from the healthcare server 106.

Further, the electronic device 101 may analyze, process, or treat bio information of the measured target, e.g., a result of monitoring a heart rate in the resting state in real-time, and output the result while simultaneously transmitting the result to the healthcare server 106, allowing a result of diagnosis or prescription according to the result to be output.

Further, the electronic device 101 may accumulate results of bio information measurement for a predetermined period necessary for health diagnosis and may store the accumulated bio information measurement data in the memory 130. The accumulated bio information measurement data may be transmitted to the healthcare server 106. The healthcare server 106 may allow for comprehensive support on various heath state information, diagnosis results, the search for various medical information, customers' health promotion, self-diagnosis, medical service appointments, information of comparing and evaluating various products, and information on clinics, based on the received bio information measurement data.

When the diagnosis result shows an emergency, e.g., when a width of a variation in heart rate in the resting state is greater than or equal to a predetermined level, the healthcare server 106 or the electronic device 101 may inform the user of the emergency so that the user may take emergency measures. As such, the healthcare server 106 may collect, generate, store, provide, or process the bio information that is based on the measured biological signal and send the result back to the user through the electronic device 101.

According to an embodiment of the present disclosure, the network 162 may be a telecommunication network. The telecommunication network may include a computer network, the Internet, an Internet of things (IoT) network, or a telephone network, or any combination of the foregoing. According to an embodiment of the present disclosure, protocols for communication between the electronic device 101 and the external electronic device (examples of such protocols include, but not limited to, transport layer protocol, data link layer protocol, or physical layer protocol) may be supported by the application 134, the API 133, the middleware 132, the kernel 131, or the communication interface 160.

The sensor module 170 may include at least one sensor for detecting the state of the electronic device 101. For example, the sensor module 170 may include a proximity sensor to detect whether the user approaches the electronic device 101 and a motion sensor to detect a motion or movement of the electronic device 101. Here, the motion sensor may output a sensing data value according to a movement of the electronic device 101. According to an embodiment of the present disclosure, the motion sensor may include an acceleration sensor to detect the acceleration of the electronic device 101. Here, the acceleration sensor may be a two-dimensional (X axis and Y axis) or three-dimensional (X axis, Y axis, and Z axis) acceleration sensor.

The sensor module 170 may further include at least one of an illumination sensor to detect the amount of light around the electronic device 101, a motion sensor to detect an operation of the electronic device 101, a gyroscope to detect the rotation of the electronic device 101, a geomagnetic sensor to detect an orientation (point of the compass) of the electronic device 101 using a geomagnetic field, a gravity sensor to detect the direction in which the gravity acts, and an altimeter to measure an air pressure to detect the altitude.

Further, the sensor module 170 may include a bio sensor. The bio sensor may measure various biological signals for the user wearing the electronic device 101 and output bio sensor values respectively corresponding to the biological signals. According to an embodiment of the present disclosure, the bio sensor may include a heart rate sensor to measure the user's heart rate. It is noted that the heart rate can be measured by measurement of a pulse. Accordingly, as used herein, "heart rate" shall include "pulse." As the heart rate sensor, a piezoelectric sensor or photoelectric sensor may come in use. Further, the bio sensor may include at least one of a galvanic skin response (GSR) sensor or a temperature sensor. According to an embodiment of the present disclosure, the bio sensor may be used to determine whether the electronic device 101 is being worn on the user's body as well as to measure various biological signals of the user. According to an embodiment of the present disclosure, in order to determine whether the electronic device 101 is being worn on the user's body, the bio sensor may be activated or the proximity sensor to detect whether the user approaches the 101 may be activated. Or, two or more sensors, such as the bio sensor or proximity sensor, may be activated.

According to an embodiment of the present disclosure, when the electronic device is determined through the proximity sensor to approach or contact a portion of the user's body, the acceleration sensor may be used to produce a movement value of the electronic device 101 and to determine a resting time when the movement value is maintained for a predetermined time period within a predetermined threshold range to activate the bio sensor at the resting time. Here, the bio sensor may be activated at the resting time when the movement value is determined to be maintained for the predetermined time period within the predetermined first threshold range. Alternatively, the bio sensor may be activated at the time when the movement value comes in the predetermined first threshold range. As such, the bio sensor, e.g., the heart rate sensor, may be activated at the time when it is determined that there is no movement. Thus, a heart rate measurement result in the resting state may be obtained.

Each of the aforementioned components of the electronic device may include one or more parts, and a name of the part may vary with a type of the electronic device. The electronic device in accordance with various embodiments of the present disclosure may include at least one of the aforementioned components, omit some of them, or include other additional component(s). Some of the components may be combined into an entity, but the entity may perform the same functions as the components may do.

The term 'module' may refer to a unit including one of hardware, memory storing executable instructions, a computer-readable medium having executable instructions embedded thereon, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, the module may include at least one of Application Specific Integrated Circuit (ASIC) chips, Field Programmable Gate Arrays (FPGAs), or Programmable Logic Arrays (PLAs) that perform some operations, which have already been known or will be developed in the future.

At least a part of the device (e.g., modules or their functions) or method (e.g., operations) may be implemented as instructions stored in a computer-readable storage medium e.g., in the form of a programming module. The instructions, when executed by one or more processor (e.g., the processor 120), may cause the processor to carry out a corresponding function. The computer-readable storage medium may be e.g., the memory 130. At least a part of the programming module may be implemented (e.g., executed) by e.g., the processor 120. At least a part of the programming module may include e.g., a module, program, routine, set of instructions, process, or the like for performing one or more functions.

The computer-readable storage medium may include a hardware device configured to store and perform program instructions (e.g., programming module), such as magnetic media such as hard discs, floppy discs, and magnetic tapes, optical media such as compact disc read only memories (CD-ROMs) and digital versatile discs (DVDs), magneto-optical media such as floptical disks, read only memories (ROMs), random access memories (RAMs), flash memories, and/or the like. Examples of the program instructions may include not only machine language codes but also high-level language codes which are executable by various computing means using an interpreter. The aforementioned hardware devices may be configured to operate as one or more software modules to carry out exemplary embodiments of the present disclosure, and vice versa.

Figure 2:
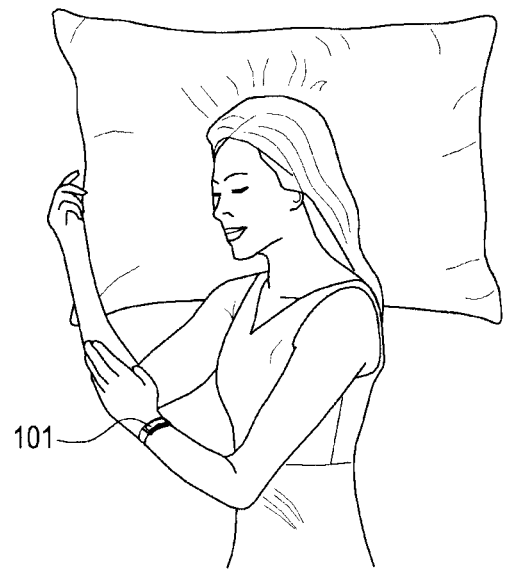
FIG. 2 is a view illustrating an example of monitoring a heart rate in a resting state by an electronic device according to an embodiment of the present disclosure.

FIG. 2 is a view illustrating an example of monitoring a heart rate in a resting state by an electronic device according to an embodiment of the present disclosure.

Referring to FIG. 2, the electronic device 101 may be worn by the user. The electronic device 101 may monitor the user's condition or state while worn by the user. The electronic device 101 may be put on a portion of the user's body, such as face, wrist, arm, head, or ankle. While put on the portion of the user's body, the electronic device 101 may be able to monitor the heart rate even in sleep. Therefore, the user's heart rate in the resting state may be automatically measured whenever the motionless state lasts for a predetermined time even while the user does his daily routines, eliminating the need of forcedly leaving himself in the lying position before wakeup to measure a resting heart rate. As such heart rate measurement results accumulate for a predetermined time period, the result of monitoring resting heart rates becomes more reliable.

Figure 3:
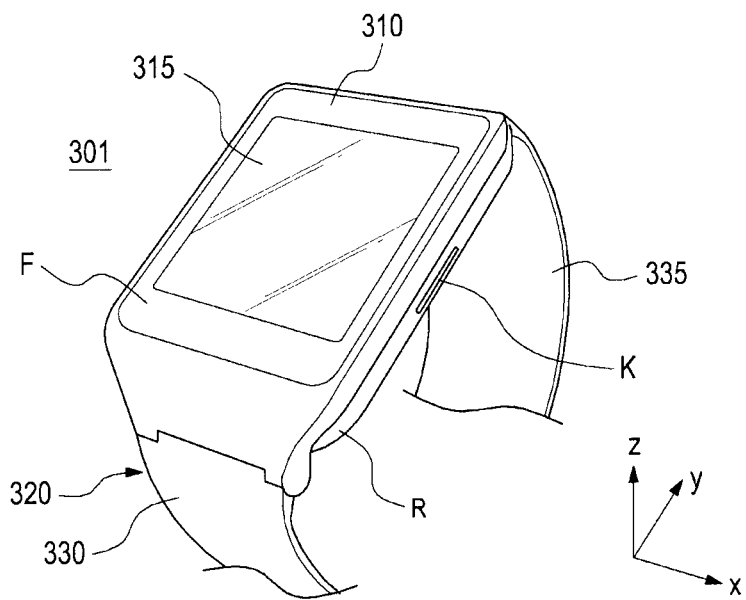
FIG. 3 is a perspective view illustrating an example where an electronic device is worn according to an embodiment of the present disclosure.

FIG. 3 is a perspective view illustrating an example where an electronic device is worn according to an embodiment of the present disclosure. Referring to FIG. 3, a three-dimensional X/Y/Z orthogonal coordinate system is shown. The "Z" axis refers to an upper-lower direction (thickness direction) of the main body 310 of the electronic device 301, the "X axis" a horizontal direction of the main body 310, and the "Y axis" a vertical direction of the main body 310.

According to an embodiment of the present disclosure, the electronic device 301 may be an electronic device that may be worn like, e.g., a watch, armband, hair band, or bracelet. However, embodiments of the present disclosure are not limited thereto. For example, the electronic device may be one of an anklet, a strip, a band, an adhesive (Band-Aid type) band, a belt, an ear-worn earphone, a headphone, a clothes-type device, a shoe-type device, a head mounted display (HMD), a hat-type device, a glove-type device, a thimble (fingertip-worn) device, a clip-type device, an armband-type device, a contact lens device, a digital clothing device, or a remote controller.

Further, according to an embodiment of the present disclosure, the electronic device may apply to a curved part of the user's body in a diversified manner. The curved part of the user's body may be, e.g., a wrist or ankle. According to an embodiment of the present disclosure, the electronic device may be easily put on various parts of the user's body depending on the configuration of a wearing unit.

According to an embodiment of the present disclosure, the electronic device 301 may include the main body 310 (a function device portion) and a wearing portion 320 including a wearing member (e.g., a band or strap). The main body 310 may be detachably coupled to the wearing portion 320. On the main body 310 may be arranged a display 315 to display various types of information, a pressing key (e.g., a side key K) to enter various types of information, a sensor module (e.g., a bio sensor), or a touch input unit. The main body 310 may include a front surface F and a rear surface R contacting the user's body when the electronic device is worn on the user). The display 315 may be positioned on the front surface F of the main body 310, and the sensor module may be positioned on the rear surface R of the main body 310.

The main body 310 may be shaped as a bar and may at least partially have a curvature corresponding to the user's body. For example, the main body 310 may be shaped substantially as a rectangle extending in the vertical direction (the Y axis direction) with a curvature. The main body 310 may have a connecting hole on its side for coupling with the wearing portion 320.

The wearing portion 320 may be formed of an elastic material and enables the main body 310 to be stably worn on the user's body. As necessary, the wearing portion 320 may bring the main body 310 in snug contact with the user's skin. The main body 310 may be detachably coupled to the wearing portion 320. Accordingly, the wearing portion 320 may be adjusted by the user's taste or preference. According to an embodiment of the present disclosure, the portion of the wearing portion 320 that is coupled to the main body 310 may be configured to be elastically transformed, and the worn surface (e.g., the inner surface of the first and second wearing members 330 and 335) brought in snug contact with the user's body might not be formed of an elastic material. The wearing portion 320 may have an opening extending in a direction thereof and where the main body 310 is fitted or removed.

The first and second wearing members 330 and 335 may extend apart from each other along the vertical direction (Y) of the main body 310. However, the first and second wearing members 330 and 335 may have a curved shape along the thickness direction (Z) of the main body 310 considering that the electronic device 301 is worn on the user's body.

The wearing portion 320 may include a means to together couple the first and second wearing members 330 and 335. For example, as the first wearing member 330 and the second wearing member 335 are tied together, the wearing portion 320 may be left in a closed curve shape. The wearing portion 320, when configured to have an exchangeable structure, may be implemented to have various designs or colors and may be replaced by the user's taste. That is, the wearing portion 320 may be utilized as a fashion accessory.

Figure 4A:
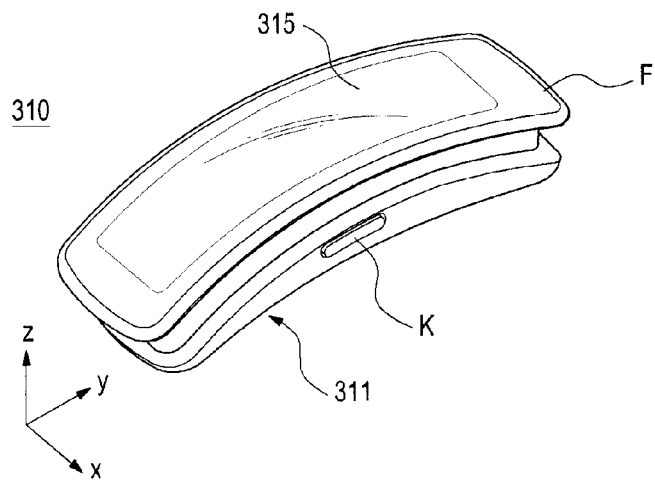
FIG. 4A is a perspective view illustrating a main body of an electronic device according to an embodiment of the present disclosure.
Figure 4B:
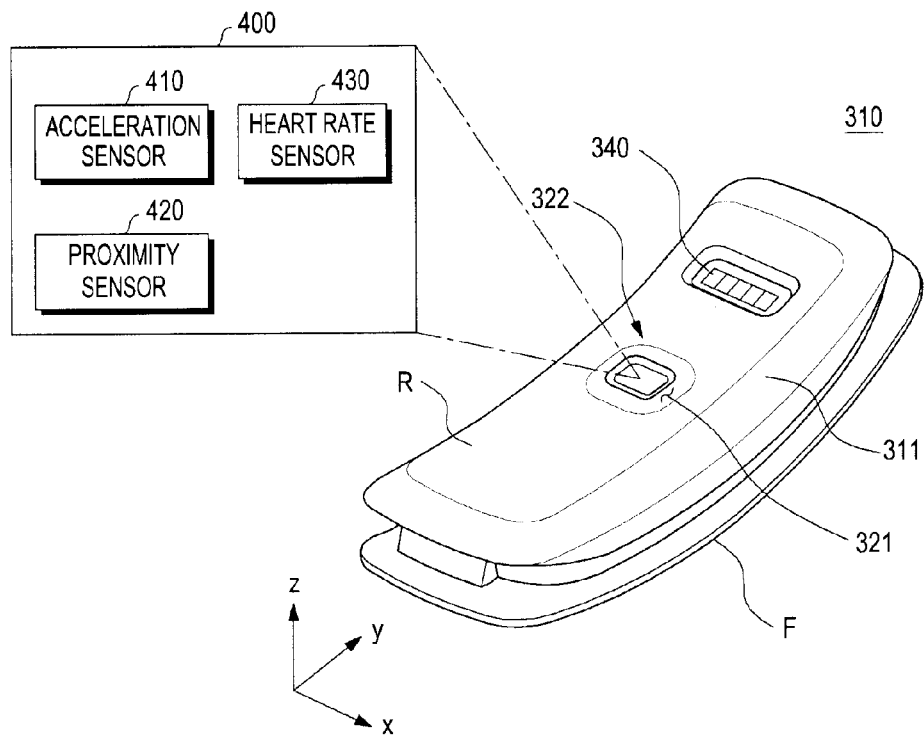
FIG. 4B is a perspective view illustrating the main body of the electronic device as viewed in a different direction according to an embodiment of the present disclosure.

FIG. 4A is a perspective view illustrating a main body of an electronic device according to an embodiment of the present disclosure. FIG. 4B is a perspective view illustrating the main body of the electronic device as viewed in a different direction according to an embodiment of the present disclosure.

Referring to FIGS. 4A and 4B, the main body 310 may include a body housing 311 and a display 315 mounted on the body housing 311. The body housing 311 may include a front surface F, a rear surface R, and a side surface connecting the front surface F with the rear surface R. The front surface F and the rear surface R each may be configured with a curvature. The main body 310 may further include a pressing key (e.g., a side key K) to enter various types of information. The front surface F is a surface on which the display 315 is positioned, and the rear surface R is a surface that contacts the user's body. The front surface F has a first curvature, and the rear surface R has a second curvature. The first and second curvatures may be determined considering the design of the product, the outline of the user' wrist, and the sense of wearing. FIGS. 4a and 4b illustrate an example in which the first curvature is smaller than the second curvature. Although in the instant embodiment the rear surface R has the second curvature, the rear surface R may alternatively be formed to be flat overall or partially.

The front surface F of the body housing 311 has the display 315 disposed thereon and needs to be configured to enable easier screen viewing. The rear surface R of the body housing 311 should be configured to provide a comfortable fit. Since a sensor module 400 (e.g., a bio sensor) is disposed on the rear surface R, the rear surface R may have a shape to tightly contact the user's wrist.

The body housing 311 may have a curvature suited for the user's body shape, e.g., the thickness or curvature (e.g., the second curvature) of the wrist, thus enhancing wearability and increasing compatibility with various customers. The curved display 315 may be provided on the front surface F of the body housing 311, and the sensor module 400, e.g., a bio sensor, may be provided on the rear surface R of the body housing 311. The rear surface R may come in contact with the user's body (e.g., a wrist). As set forth above, the body housing 311 may be shaped to have a curvature considering the user's body shape and allows the sensor module 400 to come in snug contact with the user's body.

The sensor module 400 provided on the body housing 311 may include at least one of an acceleration sensor, a heart rate sensor, a proximity sensor, a photo sensor, a GSR sensor, and a temperature sensor (such as a thermometer). The sensor module 400 may include other various sensors to determine whether the electronic device 301 is worn. Although the display 315 is shown to have a shape reflecting the user's body curvature, the display 315 may alternatively be configured as a flat display (e.g., a liquid crystal display (LCD) or an organic light emitting diode (OLED) display), a curved display, or a flexible display. For example, although in the instant embodiment the main body 310 has a curved display, the main body 310 may alternatively have a flat display or a flexible display.

A protrusion 322 may be formed on the rear surface R of the main body 310 to allow the sensor module 400 to more snugly contact the user's body. The sensor module 400 may be positioned on the protrusion 322. Contact members 340, e.g., recharging terminals, may be arranged on the rear surface R of the main body 310. The array of the contact members 340 may be positioned adjacent to the sensor module 400.

Referring to FIG. 4B, the sensor module 400 may be provided on the rear surface R of the body housing 311 in the form of a single module including an acceleration sensor 410 to measure a movement of the electronic device 301, a sensor used to determine whether the electronic device is worn on the body, e.g., the proximity sensor 420, and a bio sensor, e.g., the heart rate sensor 430, to measure a biological signal.

The sensor module 400 may include a sensor interface 321, e.g., an interface window, disposed on the rear surface R of the main body 310. To place the sensor interface 321, the protrusion 322 may be formed on the rear surface R. As the sensor interface 321 is disposed on the protrusion 322, the sensor module 400 may come in more snug contact with the user's body when sensing a biological signal.

According to an embodiment of the present disclosure, the acceleration sensor 410 may be a two-dimensional (X axis and Y axis) or three-dimensional (X axis, Y axis, and Z axis) acceleration sensor. According to an embodiment of the present disclosure, the proximity sensor 420 may be used to determine whether the electronic device is worn on the body, and the proximity sensor 420 may detect whether an object, e.g., the user's wrist, approaches an inner surface of the electronic device 301. Here, while the proximity sensor 420 may detect an object approaching the inner surface of the electronic device 301, at least one bio sensor may be activated to determine whether the approaching object is actually the user's body.

The proximity sensor 420 may come in various types depending on detection schemes, and among them, may include an optical-type photo sensor, such as an infrared ray (IR) sensor.

The photo sensor may convert light itself or information included in light into an electric signal. The photo sensor may include a light emitting portion and a light receiving portion. The photo sensor may emit light through the light emitting portion and receive light through the light receiving portion. The photo sensor may come close or contact a portion of the user's body when the electronic device 301 is worn on the user's body. When the photo sensor comes close or contacts the portion of the user's body, light emitted from the light emitting portion may be radiated to the user's body, and a reflection from the user's body may be received by the light receiving portion. The photo sensor may measure and output the amount of the reflection received by the light receiving portion. The amount of light measured may be used to determine whether the photo sensor comes close or contacts the portion of the user's body, and whether the photo sensor comes close or contacts the portion of the user's body may be used to determine whether the electronic device 301 is worn on the user's body.

According to an embodiment of the present disclosure, in addition to the heart rate sensor, the sensor module 400 may include a bio sensor that may measure various biological signals of the user's body to output various bio sensor values related to the user's body and that may detect the state of wearing the electronic device. According to an embodiment of the present disclosure, the bio sensor may include at least one of a GSR sensor or a temperature sensor. The sensor module may further include other bio sensors that may determine whether the electronic device 301 is being worn on the user's body.

The GSR sensor may be a current skin resistance response sensor. The GSR sensor may be any one of an electrodermal response (EDR) sensor, a psycho galvanic reflex (PGR) sensor, or a skin conductance response (SCR). The GSR sensor may include an ohmmeter and may measure an electric conductance between two points on the skin. The GSR sensor may come close or contact a portion of the user's body when the electronic device 301 is worn on the user's body. The GSR sensor may output a skin resistance by measuring the electric conductance between the two points on the skin after applying a predetermined tiny amount of current to the user's skin when approaching or contacting the portion of the user's body. The electric conductance measured may be used to determine whether the GSR sensor comes close or contacts the portion of the user's body, and whether the GSR sensor comes close or contacts the portion of the user's body may be used to determine whether the electronic device 301 is worn on the user's body.

The temperature sensor may be a sensor that measures a temperature based on variations of electrical resistance, voltage or current that is made when the temperature changes. The temperature sensor may come close or contact a portion of the user's body when the electronic device 301 is worn on the user's body. The temperature sensor may output the value of a variation in internal resistance, voltage, or current that occurs due to the body temperature when it approaches or contacts a portion of the user's body. The measured value of the variation in internal resistance, voltage, or current may be used to determine whether the temperature sensor comes close or contacts the portion of the user's body, and whether the temperature sensor comes close or contacts the portion of the user's body may be used to determine whether the electronic device 301 is worn on the user's body.

According to an embodiment of the present disclosure, the bio sensor may include any other sensors that may measure a biological signal to determine whether the electronic device 301 is being worn on the user's body than the heart rate sensor, the GSR sensor, and the temperature sensor. For example, the bio sensor may include a heart rate variability (HRV) sensor to measure a pulse wave signal.

According to an embodiment of the present disclosure, when the proximity sensor 420 determines that the electronic device approaches or contacts a portion of the user's body, that is, while the electronic device is worn, the acceleration sensor 410 may whether a variation in the degree of movement output lasts for a predetermined time period within a predetermined interval. When the variation in the degree of movement of the electronic device 310 is maintained for the time period within the predetermined interval, the heart rate sensor may be activated. According to an embodiment of the present disclosure, the proximity sensor 420 or at least one of the bio sensors may be activated to detect the state of being worn. Or, two or more sensors may be activated. Further, other bio sensors may be included to detect a sensing value to determine whether the electronic device 301 is worn.

Figure 5:
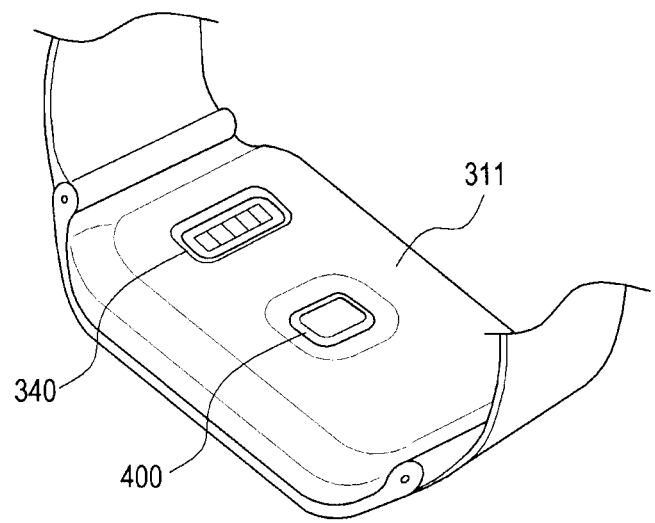
FIG. 5 and FIG. 6 are perspective views illustrating a watch-type wearable electronic device where a sensor module is positioned according to an embodiment of the present disclosure.
Figure 6:
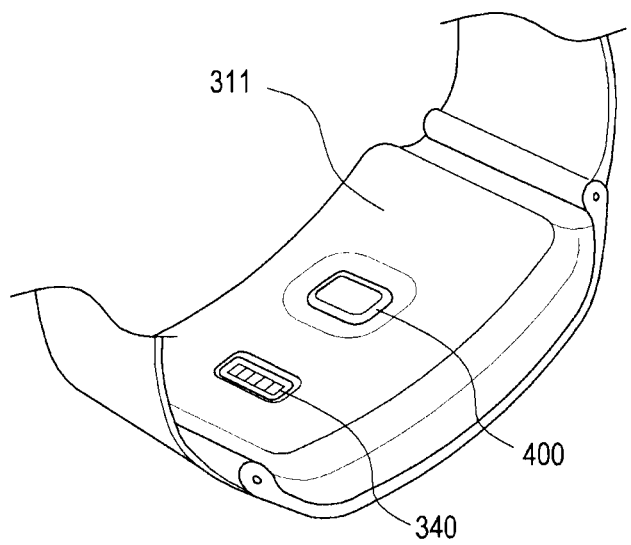

FIGS. 5 and 6 are perspective views illustrating a watch-type wearable electronic device where a sensor module is positioned according to an embodiment of the present disclosure.

Although FIG. 5 illustrates an example in which the sensor module 400 is disposed at the center of the rear surface of the substantially flat body housing 311 of the electronic device, the sensor module 400 may alternatively be disposed on an edge of the rear surface or may be disposed at any other positions where the sensor module 400 may come in contact with the user's body. Further, as shown in FIG. 6, the body housing 311 may have a predetermined curvature suited for the shape of the user's body, e.g., the thickness or curvature of the wrist, so as to come in snug contact with the user's skin. The contact members 340, e.g., recharging terminals, may be arranged adjacent to the sensor module 400.

Figure 7:
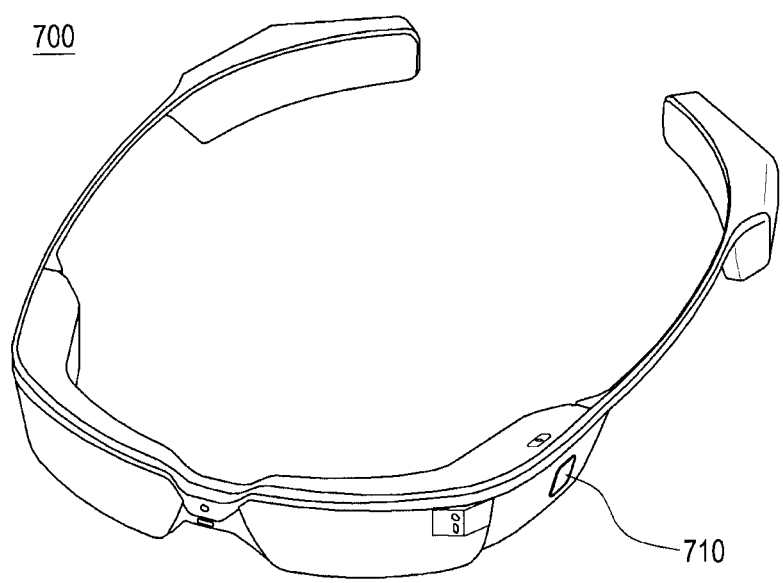
FIG. 7 is a perspective view illustrating a glasses-type electronic device where a sensor module is positioned according to an embodiment of the present disclosure.

FIG. 7 is a perspective view illustrating a glasses-type electronic device where a sensor module is positioned according to an embodiment of the present disclosure.

Referring to FIG. 7, the electronic device 700 may be implemented as a display device wearable on the user's body, e.g., face or head. A see-through display unit may be positioned in a region adjacent to the user's head (e.g., an eye), and a speaker (not shown) may be positioned in a region adjacent to the user's ear to provide the user with visual information and auditory information. The electronic device 700 may include a glasses-type display device or a helmet-type display device. The electronic device 700 may include a monocular-type display device with a single display unit for displaying content or a binocular-type display unit with a plurality of display units.

As shown in FIG. 7, a sensor module 710 may be disposed on a portion of the electronic device 700 snugly contacting the user's body (e.g., sides of the head). Although FIG. 7 illustrates an example in which the proximity sensor to sense whether the electronic device 700 is worn and the bio sensor to measure a biological signal are provided together in a region of the electronic device 700, the proximity sensor and the bio sensor may be arranged separately from each other. Accordingly, the position of the sensor module 710, e.g., the proximity sensor or the bio sensor, may be changed corresponding to the performance or structure of the electronic device 700 in order to measure a biological signal while sensing whether the electronic device 700 is worn.

Figure 8:
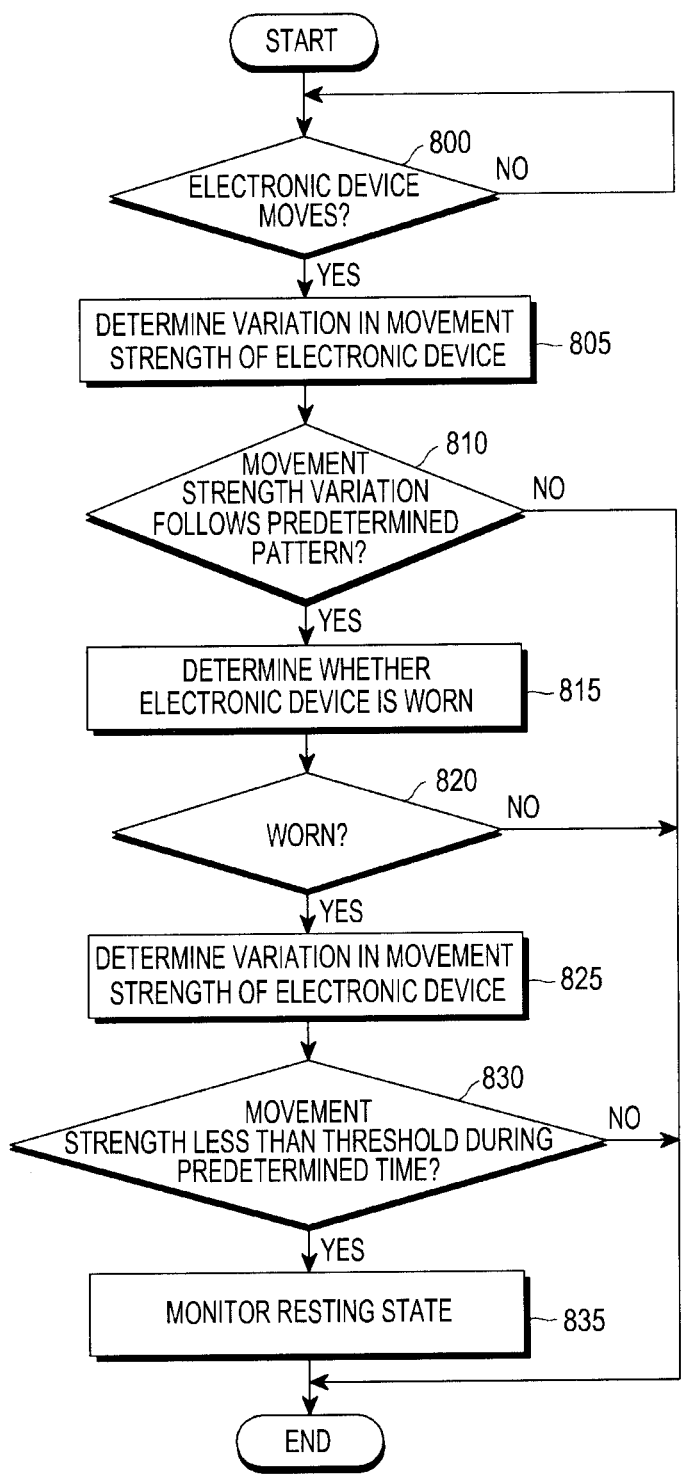
FIG. 8 is a flowchart illustrating an operation for determining a state in which an electronic device is worn according to an embodiment of the present disclosure.

FIG. 8 is a flowchart illustrating an operation for determining a state in which an electronic device is worn according to an embodiment of the present disclosure. The electronic device 101 monitors the resting state when the device is worn and when the movement strength is less than a threshold for at least a predetermined time. When the device is worn, biological signals can be measured. When the movement strength is less than the threshold for at least the predetermined time, the user is deemed to be at rest.

Referring to FIG. 8, the electronic device 101 may determine through the sensor module 170 whether a movement occurs in operation 800. When a movement occurs, a variation in movement strength of the electronic device 101 may be determined in operation 805. Here, the variation in movement strength may represent a variation history between the current degree of movement and the degree of movement that occurred a predetermined time before the current movement.

According to an embodiment of the present disclosure, the electronic device 101 may compute a movement value according to the movement of the electronic device 101 using the acceleration sensor and may compute the variation in movement strength of the electronic device 101 using the computed movement value. According to an embodiment of the present disclosure, the electronic device 101 may compute variations in movement strength in predetermined time units, e.g., one second, five seconds, or other various time units. Accordingly, the variation in movement strength may be computed at a predetermined period, e.g., ten times per second, and the period of computing the variation in movement strength may be changed.

The electronic device 101 may determine the variation in movement strength to determine whether the pattern of the variation in movement strength is a predetermined pattern in operation 810. According to an embodiment of the present disclosure, the predetermined pattern may be a pattern in which the movement strength is reduced. For example, when the user holds up the electronic device 101 on the table and puts it on his wrist, the movement strength when the electronic device 101 is held up may be larger than the movement strength when the electronic device 101 is put on. Further, the movement strength when putting on the electronic device 101 may be small as compared to holding up the electronic device 101 because of band adjustment or other manipulations to make the electronic device 101 snug with the wrist.

If during operation 810, the movement strength variation does not follow the predetermined pattern, the process is terminated.

As such, when the movement strength is reduced, the electronic device 101 may determine whether the electronic device 101 is worn in operation 815. That is, when receiving movement measurements by the sensor module 170 that are consistent with the user wearing the electronic device 101, it may be determined that the user has actually worn the electronic device 101. To that end, the electronic device 101 may determine whether the electronic device 101 is worn using the sensor module 170.

According to another embodiment of the present disclosure, the electronic device 101 may determine whether the electronic device 101 is worn using a proximity sensor. Upon using a proximity sensor provided on the rear surface of the electronic device 101, the proximity sensor on the rear surface of the electronic device 101 may determine whether a portion of the user's body has approached the proximity sensor. Whether the electronic device 101 is worn can be determined in the foregoing manner.

According to another embodiment of the present disclosure, the electronic device 101 may determine whether the electronic device 101 is worn using a GSR sensor. The GSR sensor may determine whether a portion of the user's body has contacted or approached the GSR sensor according to an electric conductance measured by the GSR sensor. Based on the electrical conductance, the electronic device 101 can determine whether it is worn.

According to an embodiment of the present disclosure, the electronic device 101 may determine whether the electronic device 101 is worn using a temperature sensor. When using the temperature sensor, the electronic device 101 may determine a portion of the user's body has approached the temperature sensor according to temperature measurements. The electronic device 101 can use the temperature measurements to determine whether it is worn. According to an embodiment of the present disclosure, the electronic device 101 may also determine which portion of the body, the electronic device 101 is being worn, e.g., the user's wrist, head, arm, ankle, or face.

If during operation 820, the device is not worn, the process terminals.

When the electronic device 101 is being worn during operation 820, the electronic device 101 may determine a movement strength of the electronic device 101 in operation 825 and may determine whether the movement strength is less than a threshold for a predetermined time in operation 830. If the electronic device 101 is being worn in operation 820, and the movement strength maintains less than the threshold for the predetermined time in operation 830, a biological signal for a resting state is measured (operation 835), and the process may come to an end.

Subsequently, when the movement strength maintains less than the threshold for the predetermined time in operation 830, which indicates that the user does not move, the electronic device 101 may perform resting state monitoring in operation 835.

As such, upon meeting both the condition that the electronic device 101 is being worn and the condition that the user does not move prior to performing the resting state monitoring, the electronic device 101 may perform such resting state monitoring in operation 835.

Since the electronic device 101 is being worn on the user's wrist, the electronic device 101 may control the sensor module 170 to measure the speed, acceleration, traveling direction, or slope of the electronic device 101. The electronic device 101 may determine the user's current state, e.g., still, running, or walking, and the posture of the user wearing the electronic device 101, e.g., the state of moving using a traveling means, based on sensing data measured through the sensor module 170 of the electronic device 101. The sensor module 170 may determine whether the user is resting by detecting where the electronic device 101 is moving slow or the state in which the user moving while wearing the electronic device 101 stops moving, at least for a predetermined time, based on the determined current state and the moving state. Here, the user's posture refers to a position of the user's body when the electronic device 101 is a body-worn electronic device. The user's posture refers to a position of the user's head when the electronic device 101 is an ear-worn electronic device. The user's posture refers to a position of the user's wrist or ankle when the electronic device 101 is a wrist-worn electronic device.

According to an embodiment of the present disclosure, whether the user is in the resting state may be determined based on the user's current state, moving state, posture, and the movement of the electronic device 101. According to an embodiment of the present disclosure, a phone use history, such as calling, call receiving, or texting, during a previous predetermined time period may also be used to determine whether the user is in the resting state. For example, even when predetermined conditions to determine the resting state, such as the movement of the electronic device 101 or the user's current state, while the electronic device 101 is worn, the electronic device 101 may trace the usage of the electronic device 101 and determine that the user is not in a resting state, when the user uses the functions such as calling/receiving or gaming for a predetermined time or more. Additionally, the electronic device 101 may determine that the user is in a resting state after functions such as using the phone or gaming come to an end.

In one embodiment, the electronic device 101 measures biological signals (e.g., the user's blood pressure, blood flow, body temperature, respiratory rate, oxygen saturation, cardiorespiratory sound, or blood sugar) when the user is at rest. The electronic device 101 determines that the user is at rest when the device is worn and there is little or no movement of the device. For example, the sensor for measuring the heart rate is activated upon determining that the user is at rest, resulting in substantially less power consumption.

Figure 9:
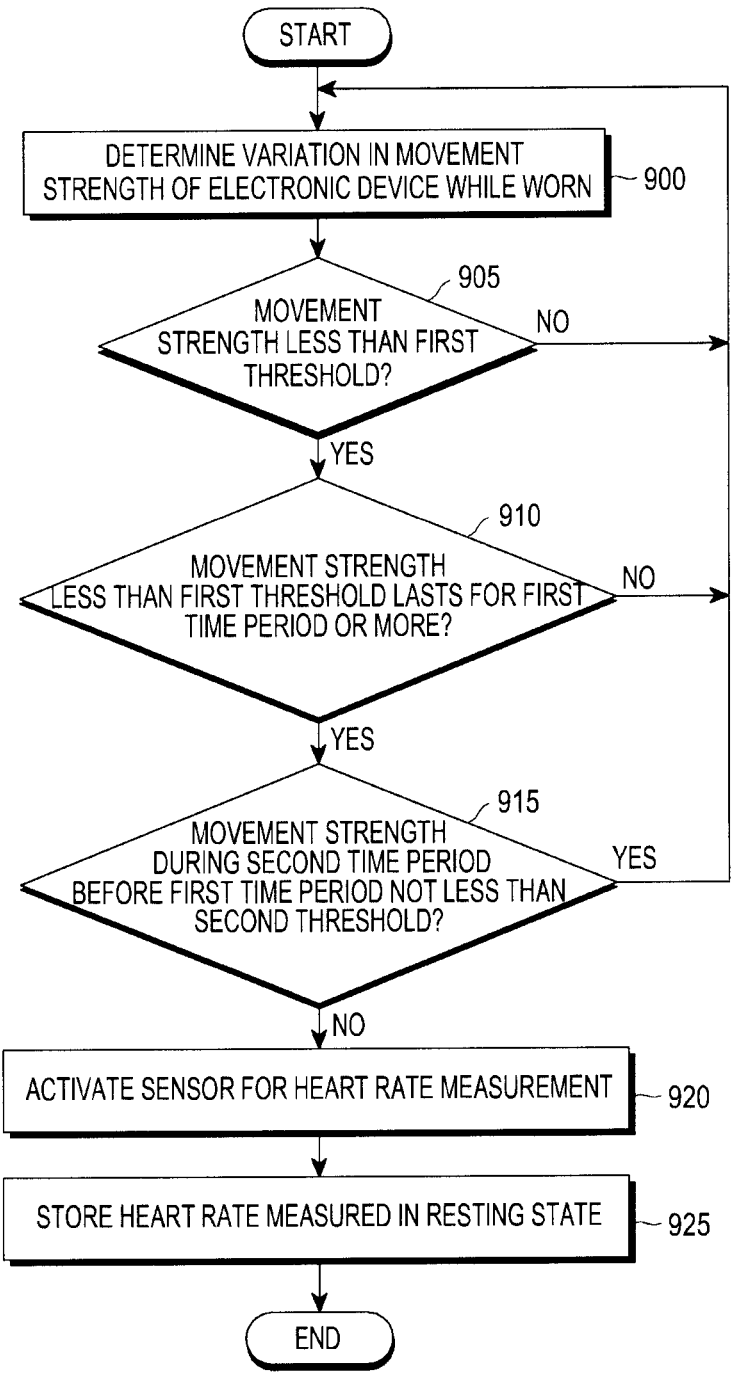
FIG. 9 is a flowchart illustrating an operation for measuring bio information in a resting state by an electronic device according to an embodiment of the present disclosure.

FIG. 9 is a flowchart illustrating an operation for measuring biological information in a resting state by an electronic device according to an embodiment of the present disclosure. For the operations shown in FIG. 9, it is assumed that the electronic device 101 is worn from the operations described above in connection with FIG. 8.

Referring to FIG. 9, the electronic device 101 may determine a variation in movement strength of the electronic device 101 through the sensor module 170 while the electronic device 101 is being worn on the user's body in operation 900. According to an embodiment of the present disclosure, the electronic device 101 may compute a movement value according to the movement of the electronic device 101 using the acceleration sensor and may compute the movement strength of the electronic device 101 using the computed movement value. Subsequently, the electronic device 101 may determine whether the computed movement strength is less than a first threshold in operation 905. When the movement strength is less than the first threshold, the electronic device 101 may determine whether the movement strength less than the first threshold lasts for a first time period or more in operation 910. When the movement strength is not less than the first threshold or when the movement strength less than the first threshold does not last for the first time period or more, the electronic device 101 may go back to operation 900.

It is noted that when the movement of the electronic device 101 is less than the first threshold, and for more than the first time period, the foregoing would normally indicate that the user is at rest. However, if this immediately follows a period of strenuous exercise, there will be a significant increase in the heart rate as compared to a routine time when the movement of the electronic device 101 being less than the first threshold, for more than the first time period. To alleviate this, the electronic device determines whether during a second time period, prior to the first time period, whether there was movement that unusually large, or larger than a second threshold, the second threshold larger than the first threshold.

Accordingly, when there is a larger movement for a second time period before the first time period, the heart rate recovery time may take longer as compared with when there is a smaller movement for the second time period. According to an embodiment of the present disclosure, the heart rate recovery time may be adjusted depending on the level of a previous movement. A method for adjusting the heart rate recovery time is described below with reference to FIGS. 10A and 10B.

When the movement strength less than the first threshold lasts for the first time period or more in operation 910, the electronic device 101 may determine whether the movement strength during the second time period before the first time period is a second threshold or more in operation 915. In other words, the electronic device 101 may determine whether there is a larger movement during the second time period before the first time period. By contrast, unless the movement strength during the second time period before the first time period is the second threshold or more, the electronic device 101 may activate a sensor for measuring a heart rate in operation 920 and store a heart rate measured in the resting state in operation 925. On the contrary, when the movement strength during the second time period before the first time period is the second threshold or more, the electronic device 101 may return to operation 900. Here, according to an embodiment of the present disclosure, when the movement during the second time period is larger, e.g., the second threshold or more, the electronic device 101 may be implemented to increase the duration of the first time period to recover the cardiac function when going back to operation 900. This is to increase the first time period, if the user has recently engaged in strenuous exercise.

As described above, according to an embodiment of the present disclosure, the electronic device 101 may measure the user's heart rates whenever meeting the condition that the state of the electronic device 101 lasts within a predetermined threshold range for a predetermined time.

According to an embodiment of the present disclosure, the user's heart rate may be measured a predetermined time after the user's state has been previously measured while the above condition is met. In other words, the electronic device 101 may return to operation 900 a predetermined time after the user's heart rate has been measured, and when the above conditions are met, may result in the measurement of a heart rate in the resting state. As such, the electronic device 101 may re-measure a heart rate when a predetermined time elapses after a previous time of heart rate measurement even when the resting state is determined to come back after the heart rate measurement, thus reducing the number of times that the heart rate sensor is activated. Thus, the energy consumption of the electronic device 101 may be reduced.

According to an embodiment of the present disclosure, when the electronic device 101 meets the above condition, a predetermined time elapses since the previous heart rate measurement was done, and the electronic device 101 is positioned so that the user is highly likely to be in the resting state in light of the user's activity pattern, and the electronic device 101 may measure the user's heart rate.

The heart rate measured only once in the above manner, or when there are multiple heart rates measured, a weighted average of the multiple heart rates may be used as a resting heart rate depending on the state and position of the electronic device 101 when the heart rates are measured.

Figure 10A:
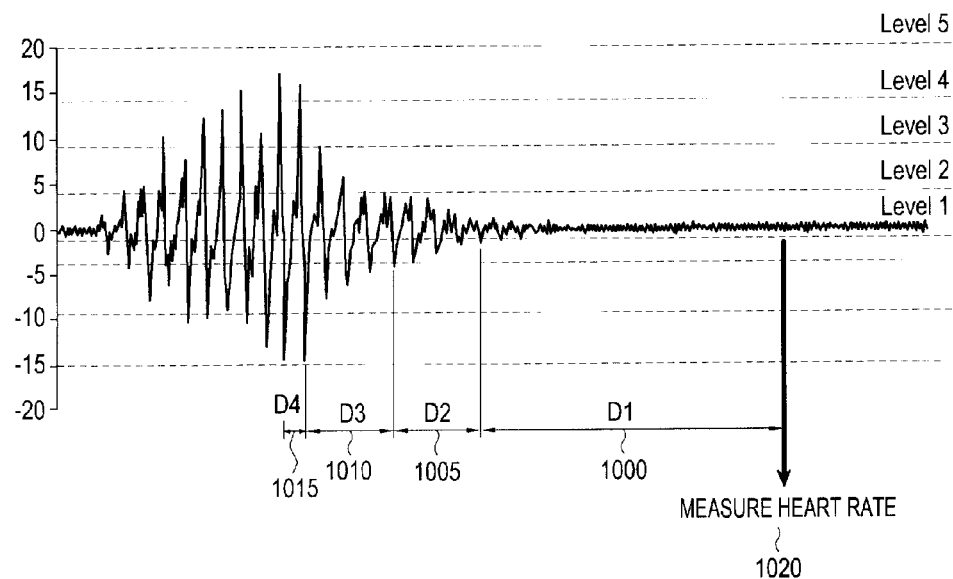
FIG. 10A and FIG. 10B are graphs illustrating movement strengths according to embodiments of the present disclosure.
Figure 10B:
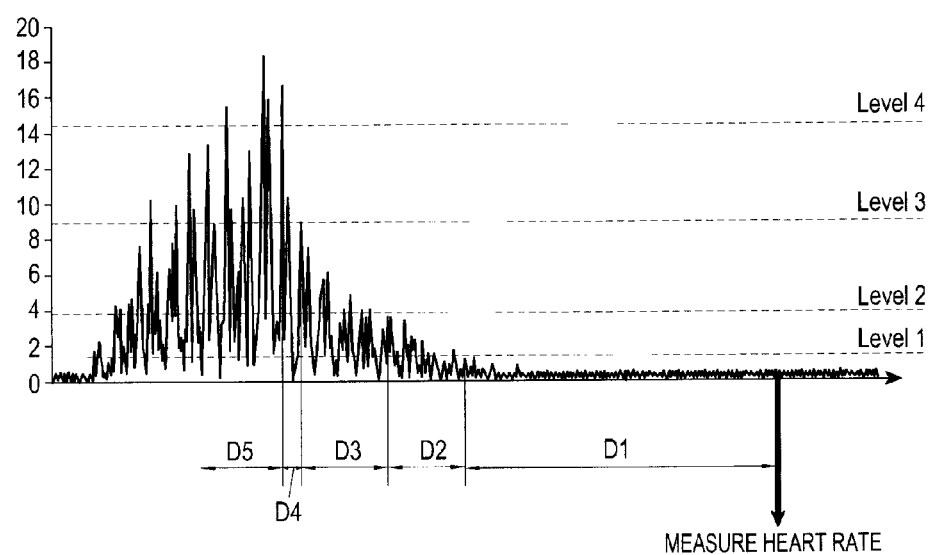

The operation of FIG. 9 is described below with reference to FIGS. 10A and 10B for better understanding. FIGS. 10A and 10B are graphs illustrating movement strengths according to embodiments of the present disclosure.

Referring to FIG. 10A, the horizontal axis (X) is a time axis, and the vertical axis (Y) is an axis indicating movement strengths. Here, the "axis indicating movement strengths" refers to a variation according to a direction of a force. For example, it may be considered that when the direction of the force is a plus (+) direction, an acceleration acts in a plus (+) direction of one of, at least, the x, y, and z axes of the acceleration sensor, and an acceleration reacts in a minus (−) direction. As shown in FIG. 10A, D1 1000 indicates a time period for determining a resting state, D2 1005 a time during which a movement strength corresponding to the user's state or a movement of the electronic device 101 is between a first threshold (e.g., Level1) and a second threshold (e.g., Level2), D3 1010 a time period during which the movement strength is between the second threshold (e.g., Level2) and a third threshold (e.g., Level3), and D4 1015 a time period during which the movement strength is between the third threshold (e.g., Level3) and a fourth threshold (e.g., Level4). Here, the width of each time period D2 to D4 may vary depending on the threshold range where the movement strength belongs.

For example, the first threshold may be a reference value for determining a state in which the user does not move so that the electronic device 101 substantially comes to a halt. According to an embodiment of the present disclosure, the first threshold may be a reference value to determine a state in which the user puts aside the electronic device 101 without wearing it. In other words, when the first threshold lasts for a predetermined time or more, the first threshold may be used to determine such a state that the user places down the electronic device 101 for, e.g., recharging, without wearing the device.

Further, the second threshold may be a reference value to determine a state in which the user wearing the electronic device 101 stops moving. According to an embodiment of the present disclosure, although the second threshold is used as a reference to determine whether the sensor for heart rate measurement is activated, for example, any other various references, such as the user's age or place or time of wearing the electronic device, or other various environmental factors, may be used as the reference value.

The third threshold may be a reference value to determine whether the state is a moving state that arises in a daily routine, the fourth threshold may be a reference value to determine whether the state is a walking state, and the fifth threshold may be a reference value to determine whether the state is a running state or engaging in strenuous exercise.

As shown in FIG. 10A, when the movement strength lasts for a predetermined time at the second threshold or less, the sensor to measure a heart rate may be activated at the time 1020 that the predetermined time has elapsed. As such, since the sensor module is activated only when required, battery consumption is reduced.

According to an embodiment of the present disclosure, when the first time period is D1 1000, the case where the movement strength during the second time period (e.g., D2 1005) before the first time period is exceeds the fourth threshold (e.g., Level4), the profile may mean that the user has engaged in more strenuous activity compared with the profile where the movement strength during the second time period is within the second threshold (e.g., Level2) range. Accordingly, time period D1 should be longer for if the time period D4 during which movement exceeded the fourth threshold (Level4) was long. Accordingly, according to an embodiment of the present disclosure, the minimum heart rate recover time as required before activating the sensor to measure a heart rate may be adjusted depending on the degree of a previous movement. In other words, the time period corresponding to D1 may be varied depending on the duration of D2 to D4. For example, the width of D1 may be more reduced when the movement strength comes in the first threshold from the fourth threshold range than when coming in the first threshold range from the second threshold range.

Meanwhile, although FIG. 10A represents movement strengths, specifically, variations in acceleration, the degree of a movement may also be recognized in a way as shown in FIG. 10B. As shown in FIG. 10A, the waveform near "0" denotes the case where the acceleration is 0, and this may occur since the waveform fluctuating between a positive value and a negative value is accelerated in the plus (+) direction by the law of action-reaction, and when put on a halt, it is accelerated in the minus (−) direction by the same law.

FIG. 10B shows magnitudes through x, y, and z values of the acceleration sensor that are shown to be larger than 0 on the graph, and such values may denote impulses. The impulses may be calculated by the following Equation 1.

$$\text{Mag} = \sqrt{x^2 + y^2 + z^2} \qquad \text{[Equation 1]}$$

In Equation 1, 'Mag' may denote an impulse, and x, y, and z may denote x, y, and z values, respectively, of the acceleration sensor.

As set forth above, the degree of a movement, i.e., a movement strength, may be determined either by a variation in acceleration as shown in FIG. 10A or by the absolute magnitude of the acceleration sensor as shown in FIG. 10B.

Figure 11A:
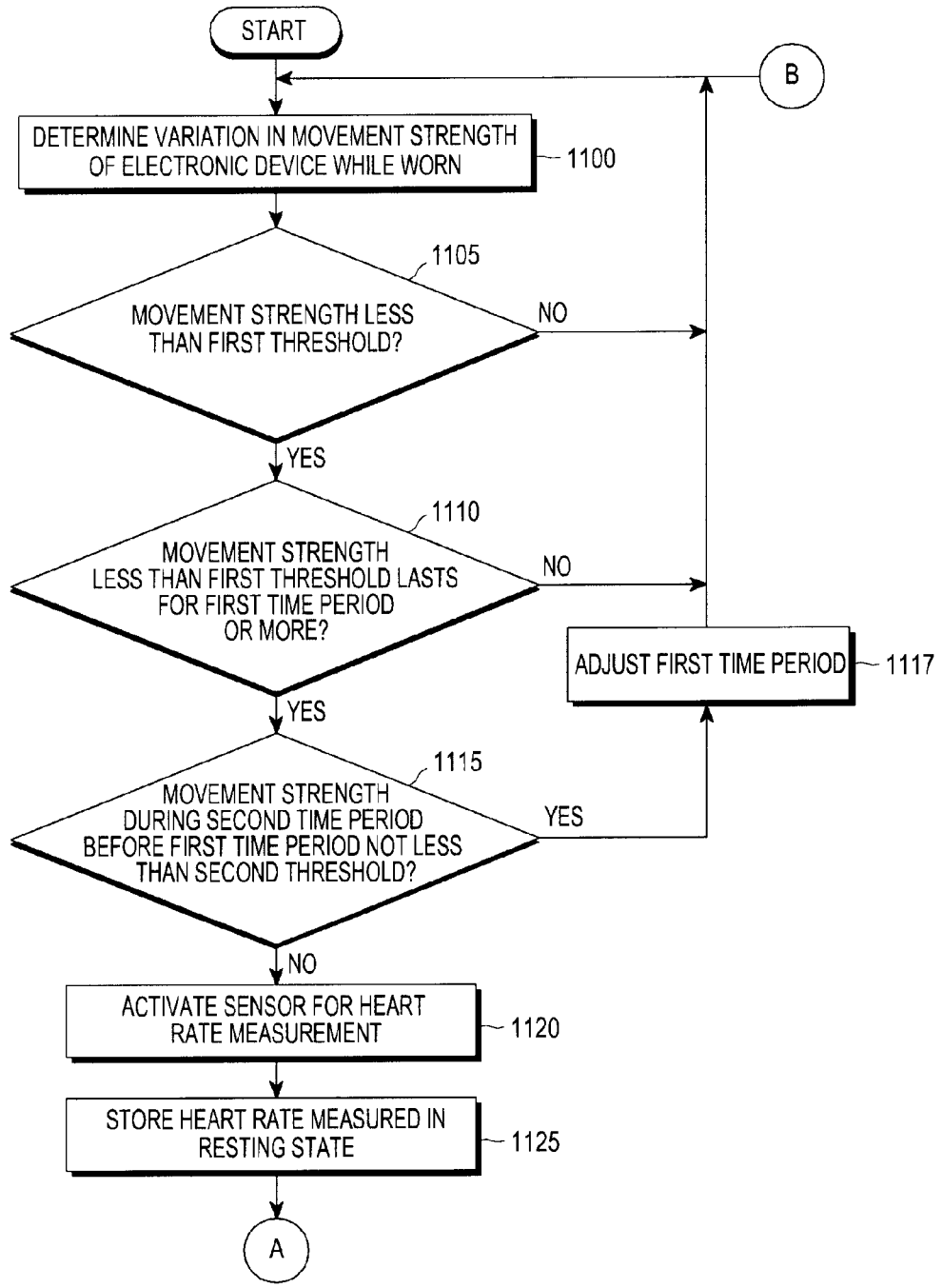
FIG. 11A and FIG. 11B are flowcharts illustrating an operation after bio information has been measured in a resting state by an electronic device according to an embodiment of the present disclosure.
Figure 11B:
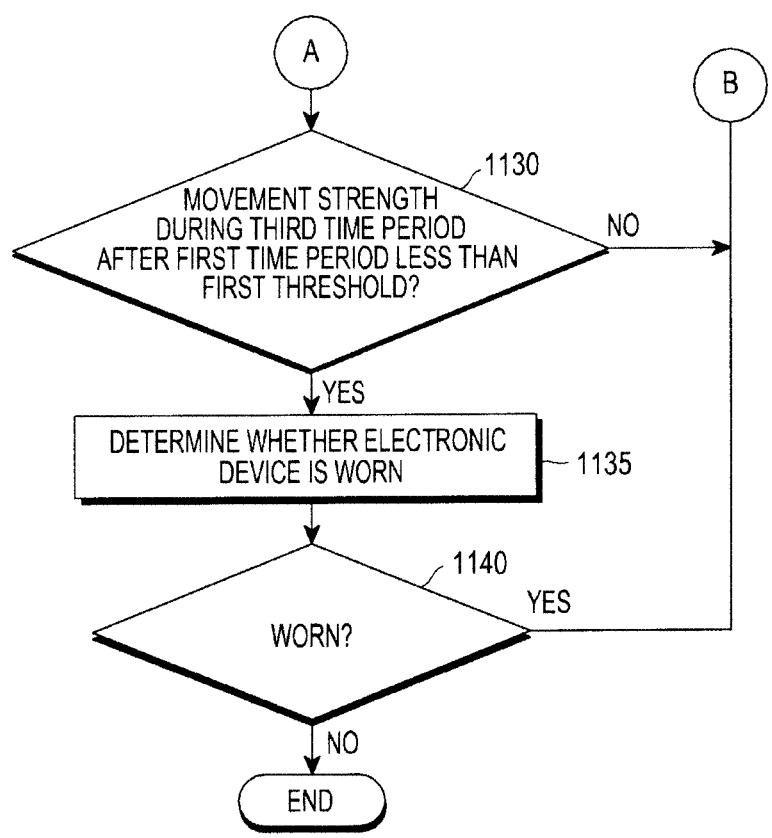

FIGS. 11A and 11B are flowcharts illustrating an operation after biological information has been measured in a resting state by an electronic device according to an embodiment of the present disclosure.

Referring to FIG. 11A, operations 1100 to 1125 are the same as operations 900 to 925 of FIG. 9, and no detailed description thereof is repeated. However, whether the movement strength is the second threshold or more during the second time period before the first time period may be determined in operation 1115. When the movement strength during the second time period before the first time period is the second threshold or more, the first time period may be adjusted considering the time required for the cardiac function to recover in operation 1117. Here, the adjusted first time period may be rendered to be longer than the previous first time period. In other words, time period D1 is made longer. Here, 'A' denotes that operation 1125 of FIG. 11A is associated with operation 1130 of FIG. 11B, and 'B' denotes that operation 1100 of FIG. 11A is associated with operation 1140 of FIG. 11B.

Thus, after activating the sensor to measure a heart rate in operation 1120 and storing a heart rate measured in the resting state in operation 1125, the electronic device 101 may determine whether the movement strength during the third time period (D3) after the first time period is less than the first threshold (Level1) in operation 1130. For example, when the user does not move with the electronic device 101 on during the first time period or does not wear the electronic device 101 so that there is no movement of the electronic device 101, the electronic device 101 may determine that the moment is a resting time to measure a heart rate in the resting state.

However, when the user thereafter takes off the electronic device 101, there may be no movement of the electronic device 101. In such case, the movement strength during the third time period may maintain less than the first threshold. Whether the electronic device 101 is worn may be determined in operation 1135 to determine whether no movement occurs since the user does not actually wear the electronic device 101. When the movement strength during the third time period is less than the first threshold, it may be determined in operation 1135 whether the electronic device 101 is worn in the same manner as operations 815 and 820 of FIG. 8. Unless the electronic device 101 is determined to be worn in operation 1140, the process may be terminated.

Figure 12:
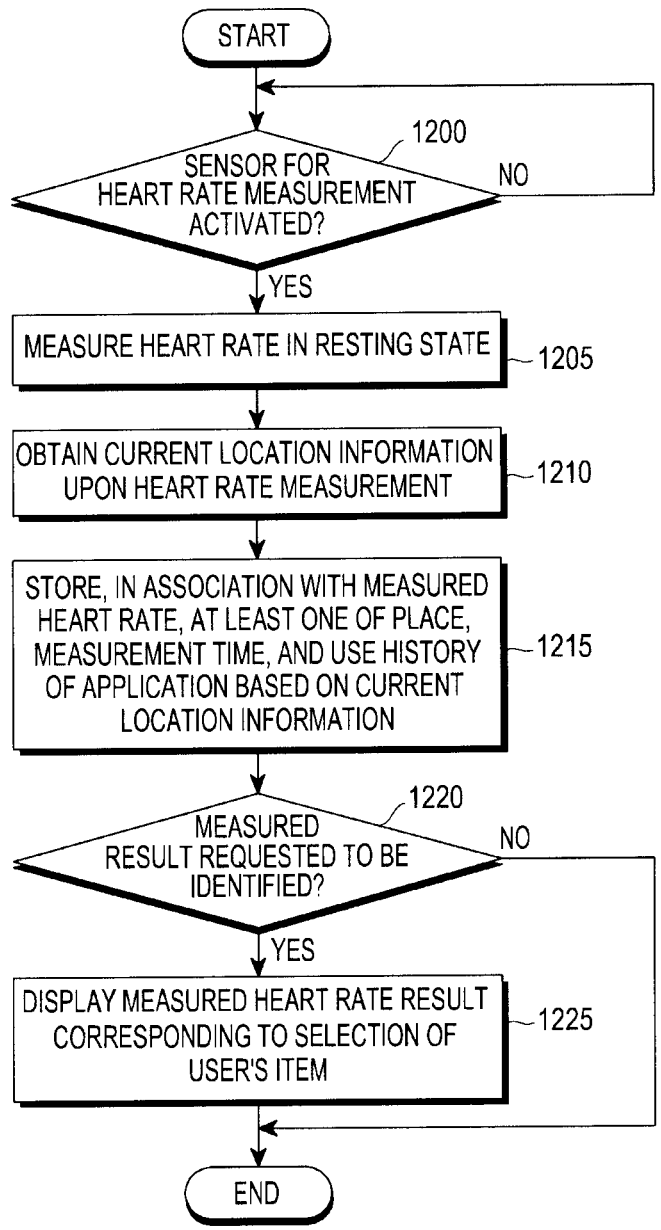
FIG. 12 is a flowchart illustrating an operation for storing a result measured based on bio information measured in a resting state by an electronic device according to an embodiment of the present disclosure.

FIG. 12 is a flowchart illustrating an operation for storing a result measured based on biological information measured in a resting state by an electronic device according to an embodiment of the present disclosure. Here, the electronic device 101 may be an electronic device that is performing monitoring to determine a resting state with the electronic device 101 worn.

Referring to FIG. 12, the electronic device 101 may determine whether the sensor to measure a heart rate is activated in operation 1200. The electronic device 101 may determine whether the resting state comes up based on, e.g., the user's moving state, the movement of the electronic device 101, or the current position, and upon determining that the resting state comes up, the electronic device 101 may activate the sensor. Accordingly, when the sensor is activated, the electronic device 101 may measure a heart rate in the resting state in operation 1205 and may obtain data to be stored together with the measured heart rate. According to an embodiment of the present disclosure, the electronic device 101 may obtain information on the current position of the electronic device 101 when measuring the heart rate in operation 1210. Subsequently, the electronic device 101 may store at least one item of place, time of measurement, and use history of application based on the current position information in association with the measured heart rate in operation 1215. Thereafter, the electronic device 101 may determine whether there is a request for identifying the measured result from the user in operation 1220. When there is the request for identifying the measured result, the electronic device 101 may display the measured heart rate result corresponding to the user's item selection in operation 1225.

Figure 13A:
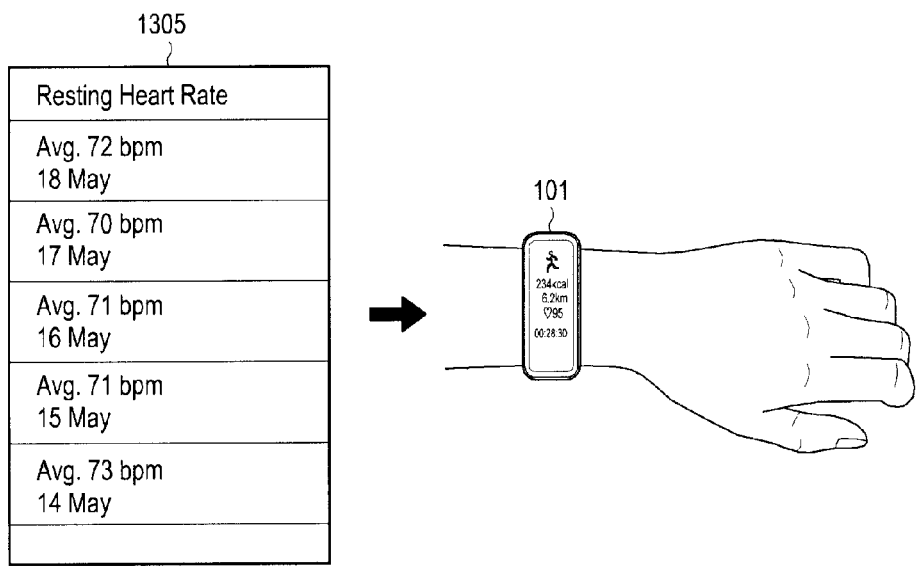
FIG. 13A, FIG. 13B and FIG. 13C are screen views illustrating results of measurement of heart rates corresponding to items selected by the user according to embodiments of the present disclosure.
Figure 13B:
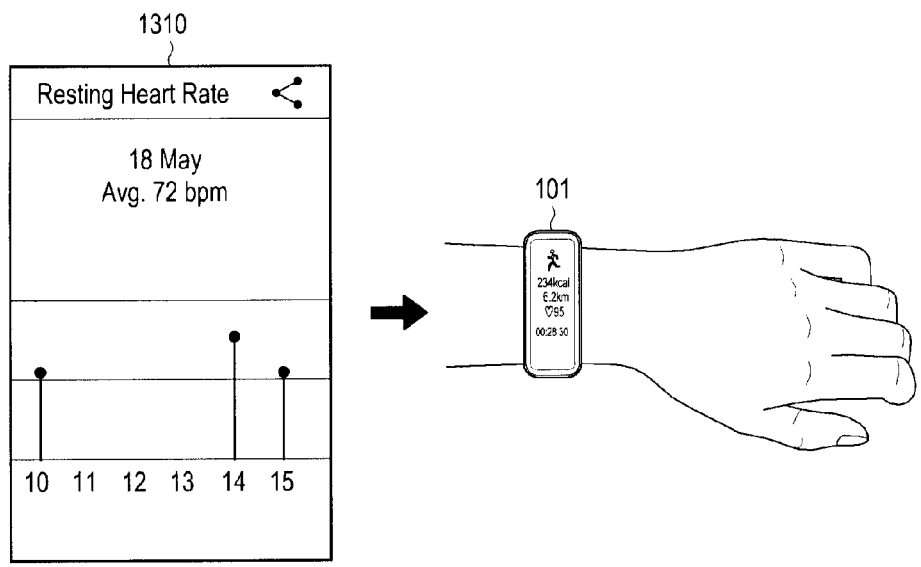
Figure 13C:
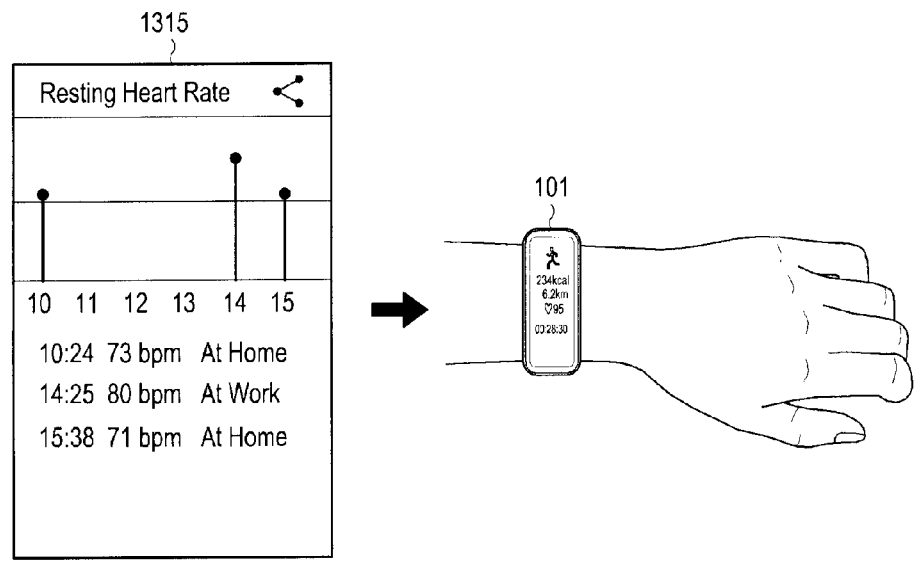

FIGS. 13A to 13C are screen views illustrating results of measurement of heart rates corresponding to items selected by the user according to embodiments of the present disclosure.

Since the electronic device 101 is being worn on the user's wrist, the electronic device 101 may determine the time when the user is in the resting state based on the sensing data measured through the sensor module 170 of the electronic device 101 and may display a resultant heart rate measured in the resting state. The resultant heart rate measured in the resting state may be stored in association with the date or time or place of the measurement.

Accordingly, when the user selects the date item as shown in FIG. 13A, the measured heart rate results 1305 in the resting state may be displayed per date on the electronic device 101. Accordingly, when the user selects the time item as shown in FIG. 13B, the measured heart rate results 1310 in the resting state may be displayed per time period on the electronic device 101. Accordingly, when the user selects the place item as shown in FIG. 13C, the measured heart rate results 1315 in the resting state may be displayed per place period on the electronic device 101. As such, the measured heart rate results may be stored in association with date or time or place of measurement, thereby leading to diversified applications. For example, the count of measuring heart rates in the resting state may be set to differ depending on whether the electronic device 101 is placed in home or work place. For example, when the user is wearing the electronic device 101 at home, his activity may be less than that while he works. Thus, a weighted frequency for heart rate measurement in the resting state may be increased considering such situation.

Meanwhile, the heart rate result measured in the resting state may be utilized for healthcare services in various manners. According to an embodiment of the present disclosure, the heart rate result measured in the resting state may be used to display a variation in the user's body condition through a tendency in which heart rates change in the resting state.

Figure 14:
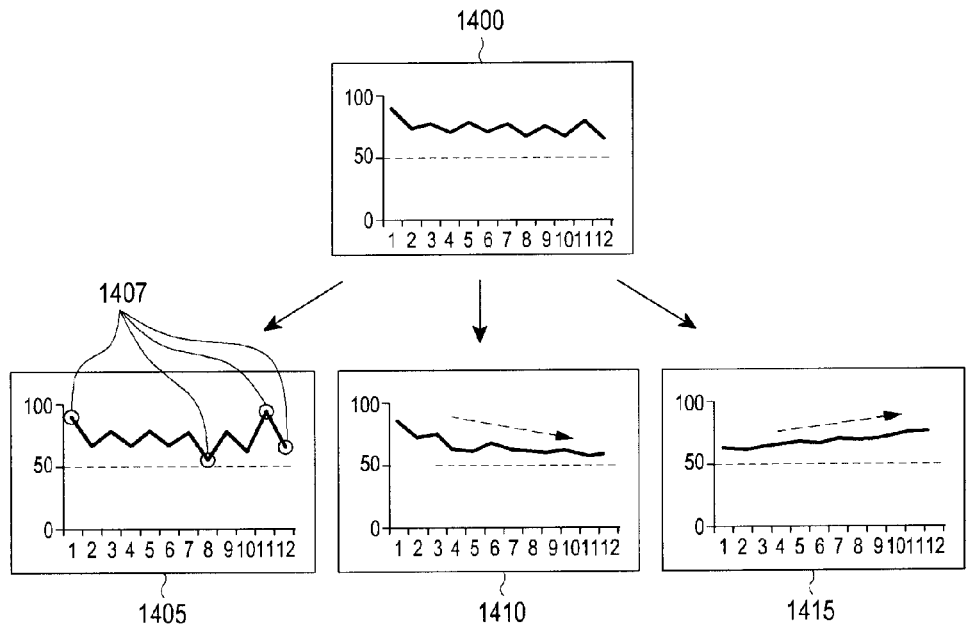
FIG. 14 is a view illustrating a healthcare service using a result of heart rate measurement performed in a resting state according to an embodiment of the present disclosure.

FIG. 14 is a view illustrating a healthcare service using a result of heart rate measurement performed in a resting state according to an embodiment of the present disclosure.

Referring to FIG. 14, when a graph 1405 with a measured heart rate of a larger width 1407 than that in a graph 1400 of heart rate results measured in the resting state and accumulated for a predetermined time period shows up, the user may be notified of the graph 1405. For example, the variation history of heart rates in the resting state may be utilized to recommend cardiography or other medical checkup for users with a variation width exceeding a predetermined standard or may be used as auxiliary material to check up the users' heart and body conditions.

Further, in the case 1410 where the heart rates automatically measured in the resting state for a predetermined time period steadily decrease as compared with the reference graph 1400, the user's health condition may be determined to gradually get better. By contrast, in the case 1415 where the user's heart rates in the resting state steadily increase, the user's health condition may be determined to gradually worsen, and its relevant feedback may be delivered to the user.

The difference between the time when the user enters the resting state based on the sensing data to measure a physical movement and the time when the user actually enters the resting state based on a heart rate may be used to determine the user's heart condition and whether there is a danger of sudden cardiac death. For example, when the user with a disease history, such as heart disease or cardiovascular disease enters the resting state but his heart rate is down to the resting state with a predetermined time or more of delay, such information may be useful to calculate the probability of the user's sudden cardiac death. Further, although it is determined that the user's movement is in the resting state while the user is wearing the electronic device 101, when the user's heart rate measured is significantly higher or lower as compared with a normal resting heart rate, it may be inferred that the user's body is in an abnormal condition. As such, when an abnormal condition occurs in the user's body, an alert may be externally transferred, so that the heart rate information in the resting state may be utilized to early discover a possible emergency. Generally, a sharply increased high heart rate may be observed if the user collapses, e.g., due to cerebral infarction, as compared with the resting heart rate measured in his routine during which he makes little or no movement. A very tiny heart rate may be observed if the user collapses, e.g., due to a faint or heart attack, as compared with the resting heart rate measured in his routine during which he makes little or no movement.

Further, the heart rate result measured in the resting state may be utilized in various manners for healthcare services other than those described above. According to an embodiment of the present disclosure, heart rate results measured in the resting state may be used to calculate calorie consumption through normalization of heart rates.

Figure 15:
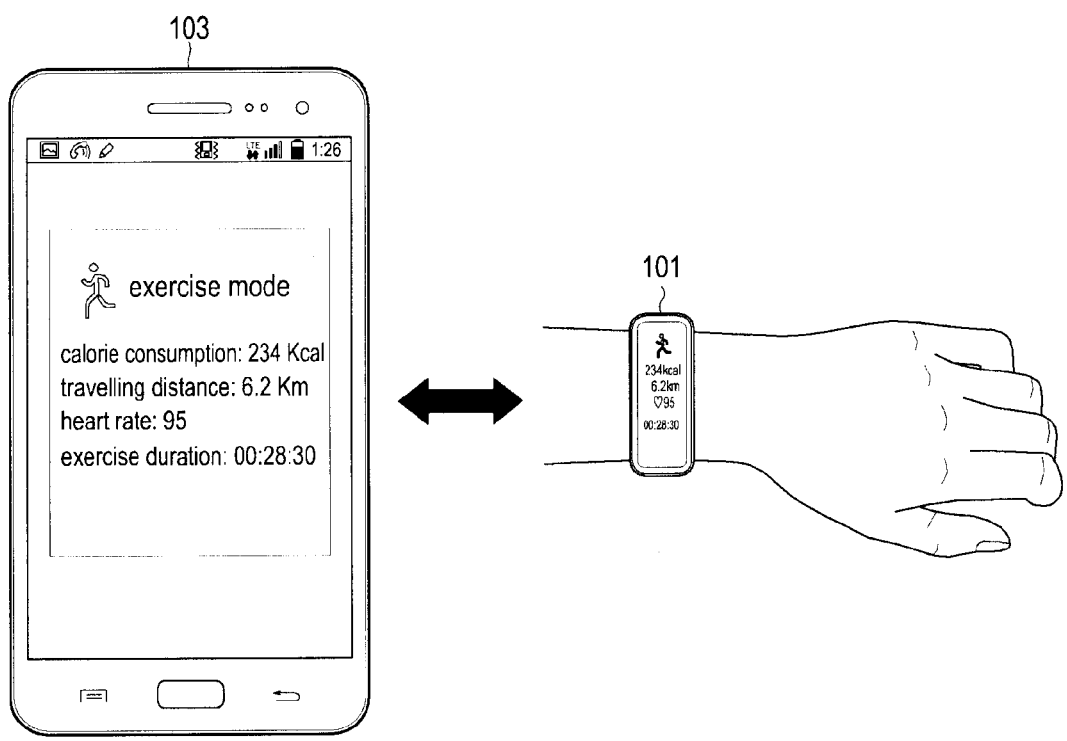
FIG. 15 is a view illustrating an example of displaying a healthcare content using a result of heart rate measurement performed in a resting state by a plurality of electronic devices according to an embodiment of the present disclosure.

FIG. 15 is a view illustrating an example of displaying a healthcare content using a result of heart rate measurement performed in a resting state by a plurality of electronic devices according to an embodiment of the present disclosure.

Referring to FIG. 15, when biological information is configured, the processor 120 of the electronic device 101 may perform control to transfer the configured biological information to another electronic device 103 communicably connected with the electronic device. In other words, the electronic device 101 may display a screen indicating that a healthcare application is running. The electronic device 101 may configure a measured heart rate result or measured heart rate result-based information for an electronic device 103 interworking with the electronic device 101 and may provide the configured information to the electronic device 103. In response, the electronic device 103 may display a healthcare screen based on a result of monitoring a heart rate in the resting state, which includes more detailed items as compared with those of the electronic device 101.

As shown in FIG. 15, the heart rate result measured in the resting state may be used to calculate calorie consumption through normalization of heart rates, and a content may be displayed according to an exercise mode based on the calorie consumption. That is, the user's calorie consumption may be calculated based on a variation in heart rate and the user's movement. Generally, as the user does a physical activity, such as exercise, his heart rate increases. The degree by which the heart rate has been increased may be used to calculate the degree of the user's physical activity and calorie consumption. Here, although the user's heart rate is increased as he attends a physical activity, the width by which the heart rate is increased may vary depending on the user's body conditions. Accordingly, the degree of the user's physical activity and calorie consumption might not be exactly calculated only with the information that his heart rate has been increased. The information on the user's heart rate in the resting state may be used to more correctly calculate his calorie consumption and degree of physical activity.

The maximum heart rate during exercise per age is generally fixed. Therefore, when the user's heart rate in the resting state is known, an available heart rate variation range per user may be obtained, and the degree by which the user's heart rate currently measured is positioned within the available heart rate variation range per user may be quantized and represented. As such, the quantized heart rate variation may be used to derive a formula for the user's calorie consumption. Here, the user's heart rate may be varied by exercise and may also be increased or decreased by strain/discomfort/ sleep/rest or other changes in his physical condition. According to an embodiment of the present disclosure, the causes for quantized heart rate variations may be differentiated using sensor information obtained from an inertia sensor, a location sensor, an air pressure sensor, a GSR sensor, or a temperature sensor, and different calorie consumption formulas may apply to their causes, thereby allowing the calorie calculation increased accuracy.

For example, when the user is determined to be in a workout, quantized heart rate variation-based calorie consumption formulas may apply depending on the state and type of the exercise, and when the user is determined to be in sleep, a calorie consumption formula optimized for a sleep state may apply to increase the accuracy of calculation of calorie consumption.

Figure 16:
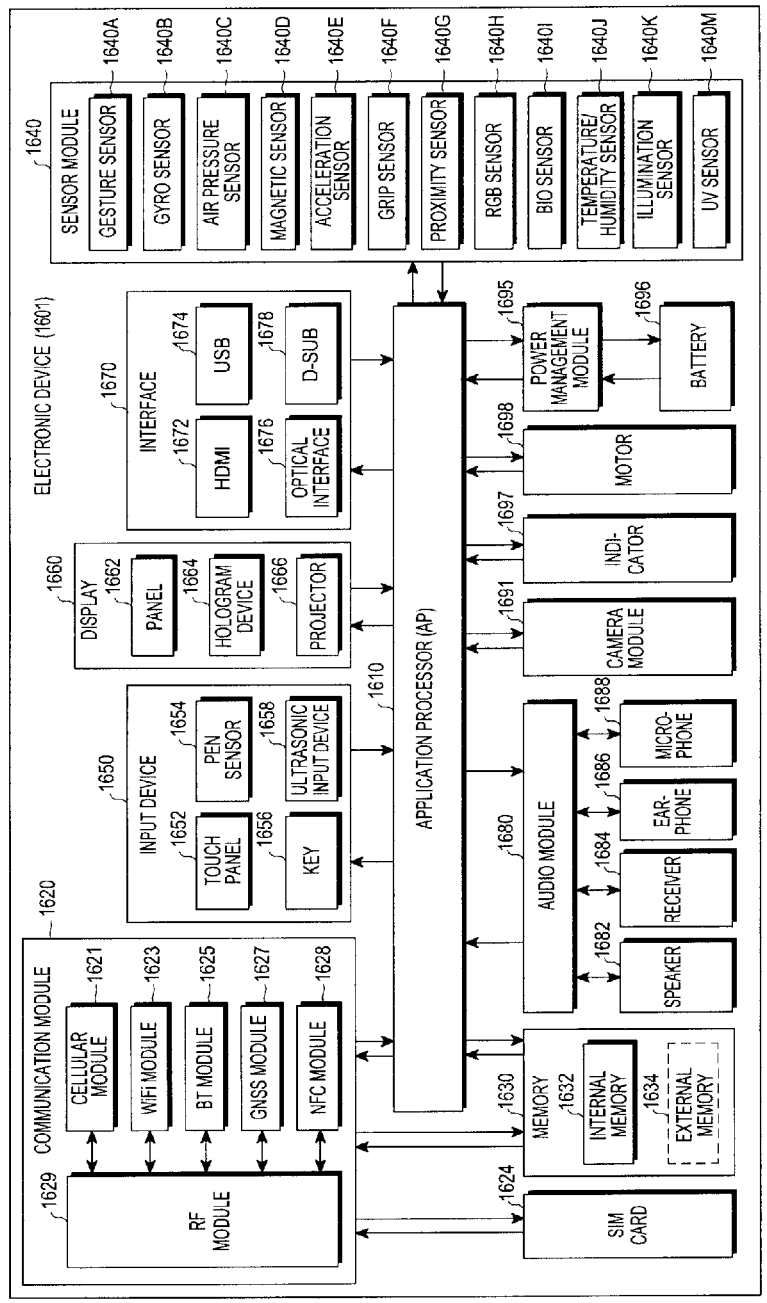
FIG. 16 is a block diagram illustrating an electronic device according to an embodiment of the present disclosure.

FIG. 16 is a block diagram illustrating an electronic device 1601 according to an embodiment of the present disclosure. The electronic device 1601 may include the whole or part of the configuration of, e.g., the electronic device 101 shown in FIG. 1. The electronic device 1601 may include one or more processors (e.g., application processors (APs)) 1610, a communication module 1620, a subscriber identification module (SIM) 1624, a memory 1630, a sensor module 1640, an input device 1650, a display 1660, an interface 1670, an audio module 1680, a camera module 1691, a power management module 1695, a battery 1696, an indicator 1697, and a motor 1698.

The processor 1610 may control multiple hardware and software components connected to the processor 1610 by running, e.g., an operating system or application programs, and the processor 210 may process and compute various data. The processor 1610 may be implemented in, e.g., a system on chip (SoC). According to an embodiment of the present disclosure, the processor 1610 may further include a graphic processing unit (GPU) and/or an image signal processor. The processor 1610 may include at least some (e.g., the cellular module 1021) of the components shown in FIG. 16. The processor 1610 may load a command or data received from at least one of other components (e.g., a non-volatile memory) on a volatile memory, process the command or data, and store various data in the non-volatile memory.

The communication module 1620 may have the same or similar configuration to the communication interface 160 of FIG. 1. The communication module 1620 may include, e.g., a cellular module 1621, a Wi-Fi module 1623, a Bluetooth module 1625, a GNSS module 1627 (e.g., a GPS module, a Glonass module, a Beidou module, or a Galileo module), an NFC module 1628, and a radio frequency (RF) module 1629.

The cellular module 1621 may provide voice call, video call, text, or Internet services through, e.g., a communication network. The cellular module 1621 may perform identification or authentication on the electronic device 201 in the communication network using a subscriber identification module 1624 (e.g., the SIM card). According to an embodiment of the present disclosure, the cellular module 1621 may perform at least some of the functions providable by the processor 1610. According to an embodiment of the present disclosure, the cellular module 1621 may include a communication processor (CP).

The Wi-Fi module 1623, the Bluetooth module 1625, the GNSS module 1627, or the NFC module 1628 may include a process for, e.g., processing data communicated through the module. At least some (e.g., two or more) of the cellular module 1621, the Wi-Fi module 1623, the Bluetooth module 1625, the GNSS module 1627, or the NFC module 1628 may be included in a single integrated circuit (IC) or an IC package.

The RF module 1629 may communicate data, e.g., communication signals (e.g., RF signals). The RF module 1629 may include, e.g., a transceiver, a power amplifier module (PAM), a frequency filter, an LNA (low noise amplifier), or an antenna. According to an embodiment of the present disclosure, at least one of the cellular module 1621, the Wi-Fi module 1623, the Bluetooth module 1625, the GNSS module 1627, or the NFC module 1628 may communicate RF signals through a separate RF module.

The subscription identification module 1624 may include, e.g., a card including a subscriber identification module and/or an embedded SIM, and may contain unique identification information (e.g., an integrated circuit card identifier (ICCID) or subscriber information (e.g., an international mobile subscriber identity (IMSI)).

The memory 1630 (e.g., the memory 130) may include, e.g., an internal memory 1632 or an external memory 1634. The internal memory 1632 may include at least one of, e.g., a volatile memory (e.g., a dynamic RAM (DRAM), a static RAM (SRAM), a synchronous dynamic RAM (SDRAM), etc.) or a non-volatile memory (e.g., a one time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash, or a NOR flash), a hard drive, or solid state drive (SSD).

The external memory 1634 may include a flash drive, e.g., a CF (compact flash) memory, an SD (secure digital) memory, a micro-SD memory, a min-SD memory, an xD (extreme digital) memory, a multi-media card (MMC), or a memory Stick™. The external memory 1634 may be functionally and/or physically connected with the electronic device 1601 via various interfaces.

For example, the sensor module 1640 may measure a physical quantity or detect an operational state of the electronic device 1601, and the sensor module 240 may convert the measured or detected information into an electrical signal. The sensor module 1640 may include at least one of, e.g., a gesture sensor 1640A, a gyro sensor 1640B, an air pressure sensor 1640C, a magnetic sensor 1640D, an acceleration sensor 1640E, a grip sensor 1640F, a proximity sensor 1640G, a color sensor 1640H such as an red-green-blue (RGB) sensor, a bio sensor 1640I, a temperature/humidity sensor 1640I, an illumination sensor 1640K, or an ultra violet (UV) sensor 1640M. Additionally or alternatively, the sensing module 1640 may include, e.g., an E-nose sensor, an electromyography (EMG) sensor, an electroencephalogram (EEG) sensor, an electrocardiogram (ECG) sensor, an infrared (IR) sensor, an iris sensor, or a finger print sensor. The sensor module 1640 may further include a control circuit for controlling at least one or more of the sensors included in the sensing module. According to an embodiment of the present disclosure, the electronic device 1601 may further include a processor configured to control the sensor module 1640 as part of the processor 1610 or separately from the processor 1610, and the electronic device 1601 may control the sensor module 1640 while the processor 1610 is in a sleep mode.

The input unit 1650 may include, e.g., a touch panel 1652, a (digital) pen sensor 1654, a key 1656, or an ultrasonic input device 1658. The touch panel 1652 may use at least one of capacitive, resistive, infrared, or ultrasonic methods. The touch panel 1652 may further include a control circuit.

The touch panel 1652 may further include a tactile layer and may provide a user with a tactile reaction.

The (digital) pen sensor 1654 may include, e.g., a part of a touch panel or a separate sheet for recognition. The key 1656 may include e.g., a physical button, optical key or key pad. The ultrasonic input device 1658 may sense an ultrasonic wave generated from an input tool through a microphone (e.g., the microphone 1688) to identify data corresponding to the sensed ultrasonic wave.

The display 1660 (e.g., the display 160) may include a panel 1662, a hologram device 1664, or a projector 1666. The panel 1662 may have the same or similar configuration to the display 160 of FIG. 1. The panel 1662 may be implemented to be flexible, transparent, or wearable. The panel 1662 may also be incorporated with the touch panel 1652 in a module. The hologram device 1664 may make three dimensional (3D) images (holograms) in the air by using light interference. The projector 1666 may display an image by projecting light onto a screen. The screen may be, for example, located inside or outside of the electronic device 1601. In accordance with an embodiment, the display 1660 may further include a control circuit to control the panel 1662, the hologram device 1664, or the projector 1666.

The interface 1670 may include e.g., a high definition multimedia interface (HDMI) 1672, a universal serial bus (USB) 1674, an optical interface 1676, or a D-subminiature (D-sub) 1678. The interface 1670 may be included in e.g., the communication interface 160 shown in FIG. 1. Additionally or alternatively, the interface 1670 may include a mobile high-definition link (MHL) interface, a secure digital (SD) card/multimedia card (MMC) interface, or IrDA standard interface.

The audio module 1680 may convert a sound into an electric signal or vice versa, for example. At least a part of the audio module 1680 may be included in e.g., the input/output interface 145 as shown in FIG. 1. The audio module 1680 may process sound information input or output through e.g., a speaker 1682, a receiver 1684, an earphone 1686, or a microphone 1688.

For example, the camera module 1691 may be a device for capturing still images and videos, and may include, according to an embodiment of the present disclosure, one or more image sensors (e.g., front and back sensors), a lens, an image signal processor (ISP), or a flash such as an LED or xenon lamp.

The power manager module 1695 may manage power of the electronic device 1601, for example. Although not shown, according to an embodiment of the present disclosure, the power manager module 1695 may include a power management integrated circuit (PMIC), a charger IC, or a battery or fuel gauge. The PMIC may have a wired and/or wireless recharging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging. The battery gauge may measure an amount of remaining power of the battery 1696, a voltage, a current, or a temperature while the battery 296 is being charged. The battery 1696 may include, e.g., a rechargeable battery or a solar battery.

The indicator 1697 may indicate a particular state of the electronic device 1601 or a part (e.g., the processor 1610) of the electronic device, including e.g., a booting state, a message state, or recharging state. The motor 1698 may convert an electric signal to a mechanical vibration and may generate a vibrational or haptic effect. Although not shown, a processing unit for supporting mobile TV, such as a GPU may be included in the electronic device 1601. The processing unit for supporting mobile TV may process media data conforming to a standard for digital multimedia broadcasting (DMB), digital video broadcasting (DVB), or mediaFlo™.

Each of the aforementioned components of the electronic device may include one or more parts, and a name of the part may vary with a type of the electronic device. The electronic device in accordance with various embodiments of the present disclosure may include at least one of the aforementioned components, omit some of them, or include other additional component(s). Some of the components may be combined into an entity, but the entity may perform the same functions as the components may do.

Figure 17:
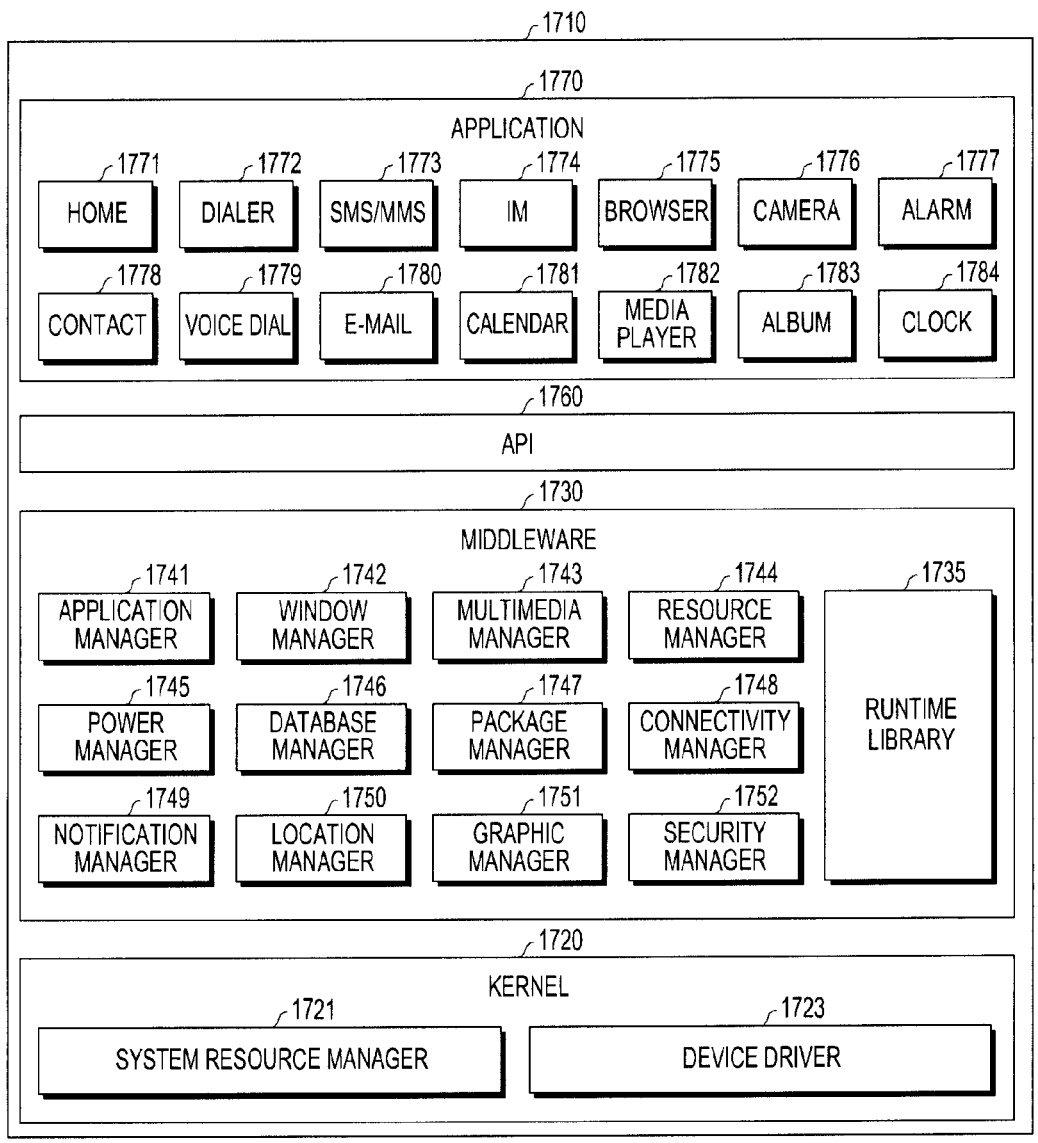
FIG. 17 is a block diagram illustrating a program module according to an embodiment of the present disclosure.

FIG. 17 is a block diagram illustrating a program module according to an embodiment of the present disclosure. According to an embodiment of the present disclosure, the program module 1710 (e.g., the program 140) may include an operating system (OS) controlling resources related to the electronic device (e.g., the electronic device 101) and/or various applications (e.g., the application processor 134) driven on the operating system. The operating system may include, e.g., Android, iOS, Windows, Symbian, Tizen, or Bada.

The program 1710 may include, e.g., a kernel 1720, middleware 1730, an application programming interface (API) 1760, and/or an application 1770. At least a part of the program module 1710 may be preloaded on the electronic device or may be downloaded from an external electronic device (e.g., the electronic devices 103 and 104 or healthcare server 106).

The kernel 1720 (e.g., the kernel 141) may include, e.g., a system resource manager 1721 and/or a device driver 1723. The system resource manager 1721 may perform control, allocation, or recovery of system resources. According to an embodiment of the present disclosure, the system resource manager 1721 may include a process managing unit, a memory managing unit, or a file system managing unit. The device driver 1723 may include, e.g., a display driver, a camera driver, a Bluetooth driver, a shared memory driver, a USB driver, a keypad driver, a Wi-Fi driver, an audio driver, or an inter-process communication (IPC) driver.

The middleware 1730 may provide various functions to the application 1770 through the API 1760 so that the application 1770 may efficiently use limited system resources in the electronic device or provide functions jointly required by applications 1770. According to an embodiment of the present disclosure, the middleware 1730 (e.g., middleware 143) may include at least one of a runtime library 1735, an application manager 1741, a window manager 1742, a multimedia manager 1743, a resource manager 1744, a power manager 1745, a database manager 1746, a package manager 1747, a connectivity manager 1748, a notification manager 1749, a location manager 1750, a graphic manager 1751, or a security manager 1752.

The runtime library 1735 may include a library module used by a compiler in order to add a new function through a programming language while, e.g., the application 1770 is being executed. The runtime library 1735 may perform input/output management, memory management, or operation on arithmetic functions.

The application manager 1741 may manage the life cycle of at least one application of, e.g., the applications 1770. The window manager 1742 may manage GUI resources used on the screen. The multimedia manager 1743 may grasp formats necessary to play various media files and use a codec appropriate for a format to perform encoding or decoding on media files. The resource manager 1744 may manage resources, such as source code of at least one of the applications 1770, memory or storage space.

The power manager 1745 may operate together with, e.g., a basic input/output system (BIOS) to manage battery or power and provide power information necessary for operating the electronic device. The database manager 1746 may generate, search, or vary a database to be used in at least one of the applications 1770. The package manager 1747 may manage installation or update of an application that is distributed in the form of a package file.

The connectivity manager 1748 may manage wireless connectivity, such as, e.g., Wi-Fi or Bluetooth. The notification manager 1749 may display or notify an event, such as a coming message, appointment, or proximity notification, of the user without interfering with the user. The location manager 1750 may manage locational information on the electronic device. The graphic manager 1751 may manage graphic effects to be offered to the user and their related user interface. The security manager 1752 may provide various security functions necessary for system security or user authentication. According to an embodiment of the present disclosure, when the electronic device (e.g., the electronic device 101) has telephony capability, the middleware 1730 may further include a telephony manager for managing voice call or video call functions of the electronic device.

The middleware 1730 may include a middleware module forming a combination of various functions of the above-described components. The middleware 1730 may provide a specified module per type of the operating system in order to provide a differentiated function. Further, the middleware 1730 may dynamically omit some existing components or add new components.

The API 1760 (e.g., the API 145) may be a set of, e.g., API programming functions and may have different configurations depending on operating systems. For example, in the case of Android or iOS, one API set may be provided per platform, and in the case of Tizen, two or more API sets may be offered per platform.

The application 1770 (e.g., the application processor 134) may include one or more applications that may provide functions such as, e.g., a home 1771, a dialer 1772, an SMS/MMS 1773, an instant message (IM) 1774, a browser 1775, a camera 1776, an alarm 1777, a contact 1778, a voice dial 1779, an email 1780, a calendar 1781, a media player 1782, an album 1783, or a clock 1784, a health-care (e.g., measuring the degree of workout or blood sugar), or provision of environmental information (e.g., provision of air pressure, moisture, or temperature information).

According to an embodiment of the present disclosure, the application 1770 may include an application (hereinafter, "information exchanging application" for convenience) supporting information exchange between the electronic device (e.g., the electronic device 101) and an external electronic device (e.g., the electronic devices 103 and 104). Examples of the information exchange application may include, but is not limited to, a notification relay application for transferring specific information to the external electronic device, or a device management application for managing the external electronic device.

For example, the notification relay application may include a function for relaying notification information generated from other applications of the electronic device (e.g., the SMS/MMS application, email application, health-care application, or environmental information application) to the external electronic device (e.g., the electronic devices 103 and 104). Further, the notification relay application may receive notification information from, e.g., the external electronic device and may provide the received notification information to the user.

The device management application may perform at least some functions of the external electronic device (e.g., the electronic device 103 or 104) communicating with the electronic device (for example, turning on/off the external electronic device (or some components of the external electronic device) or control of brightness (or resolution) of the display), and the device management application may manage (e.g., install, delete, or update) an application operating in the external electronic device or a service (e.g., call service or message service) provided from the external electronic device.

According to an embodiment of the present disclosure, the application 1770 may include an application (e.g., a healthcare application of a mobile medical device) designated according to an attribute of the external electronic device (e.g., the electronic devices 103 and 104). According to an embodiment of the present disclosure, the application 1770 may include an application received from the external electronic device (e.g., the healthcare server 106 or electronic devices 103 and 104). According to an embodiment of the present disclosure, the application 1770 may include a preloaded application or a third party application downloadable from a server. The names of the components of the program module 1710 according to the shown embodiment may be varied depending on the type of operating system.

According to an embodiment of the present disclosure, at least a part of the program module 1710 may be implemented in software, firmware, hardware, or in a combination of two or more thereof. At least a part of the programming module 1710 may be implemented (e.g., executed) by e.g., a processor (e.g., the processor 1610). At least a part of the program module 1710 may include e.g., a module, program, routine, set of instructions, process, or the like for performing one or more functions.

The term 'module' may refer to a unit including one of hardware, software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, the module may include at least one of application specific integrated circuit (ASIC) chips, field programmable gate arrays (FPGAs), or programmable logic arrays (PLAs) that perform some operations, which have already been known or will be developed in the future.

According to an embodiment of the present disclosure, at least a part of the device (e.g., modules or their functions) or method (e.g., operations) may be implemented as instructions stored in a computer-readable storage medium e.g., in the form of a program module. The instructions, when executed by a processor (e.g., the processor 120), may enable the processor to carry out a corresponding function. The computer-readable storage medium may be e.g., the memory 130.

The computer-readable storage medium may include a hardware device, such as hard discs, floppy discs, and magnetic tapes (e.g., a magnetic tape), optical media such as compact disc ROMs (CD-ROMs) and digital versatile discs (DVDs), magneto-optical media such as floptical disks, ROMs, RAMs, Flash Memories, and/or the like. Examples of the program instructions may include not only machine language codes but also high-level language codes which are executable by various computing means using an interpreter. The aforementioned hardware devices may be configured to operate as one or more software modules to carry out exemplary embodiments of the present disclosure, and vice versa.

Modules or programming modules in accordance with various embodiments of the present disclosure may include at least one or more of the aforementioned components, omit some of them, or further include other additional components. Operations performed by modules, programming modules or other components in accordance with various embodiments of the present disclosure may be carried out sequentially, simultaneously, repeatedly, or heuristically. Furthermore, some of the operations may be performed in a different order, or omitted, or include other additional operation(s). The embodiments disclosed herein are proposed for description and understanding of the disclosed technology and does not limit the scope of the present disclosure. Accordingly, the scope of the present disclosure should be interpreted as including all changes or various embodiments based on the technical spirit of the present disclosure.

As is apparent from the foregoing description, according to an embodiment of the present disclosure, the wearable electronic device may automatically measure a biological signal by detecting the user's resting state without the need of remaining still for the measurement.

According to an embodiment of the present disclosure, a sensor of the wearable electronic device may obtain a biological signal, e.g., a result of measurement of a heart rate, in a resting state where there is little variation in movement, thus leading to reduced measurement errors due to tiny movement changes and resultantly enhanced accuracy.

According to an embodiment of the present disclosure, the user's heart rate may be automatically measured based on the detection of a movement of his wearing electronic device while the user does his daily routines. Thus, heart rates in the resting state may be consecutively measured and obtained.

According to an embodiment of the present disclosure, a sensor for measuring a heart rate may be activated when the user is determined to be in a resting state based on the detection of a movement of the electronic device worn on the user. Therefore, more power savings are possible as compared with when the sensor is periodically activated.

What is claimed is:

1. A wearable electronic device, comprising:
   a first sensor configured to sense a movement of the electronic device;
   a second sensor configured to sense a biological signal for a user wearing the electronic device; and
   a processor configured to compute a movement value of the electronic device using the first sensor, to detect a resting state when the movement value lasts within a predetermined first threshold range during a first time period, and to configure biological information of the user based on the biological signal measured by the second sensor after detection of the resting state,
   wherein the processor is configured to adjust the first time period according to a movement value within a second time period before the first time period.

2. The wearable electronic device of claim 1, further comprising a third sensor configured to detect whether the user wears the electronic device.

3. The wearable electronic device of claim 2, wherein the processor is configured to compute the movement value of the electronic device using the first sensor when the third sensor detects that the user wears the electronic device.

4. The wearable electronic device of claim 1, wherein the processor is configured to write additional information related to the biological information in association with the biological information and to display together at least one of the biological information and the additional information.

5. The wearable electronic device of claim 1, wherein the processor is configured to activate the second sensor to sense the biological signal when detecting the resting state.

6. The wearable electronic device of claim 1, wherein the processor is configured to transfer the configured biological information to another electronic device communicably connected with the electronic device when the biological information is measured.

7. The wearable electronic device of claim 1, wherein the processor is configured to determine whether a movement value within a second time period before the first time period is within a second threshold range larger than the first threshold range when the movement value is within the predetermined first threshold range during the first time period, and the processor detects the resting state when the movement value within the second time period is within the second threshold range.

8. The wearable electronic device of claim 7, wherein the processor increases the first time period when the movement value within the second time period exceeds the second threshold range.

9. The wearable electronic device of claim 4, wherein the additional information includes at least one of a date, time, or place of the measurement of the biological signal.

10. A method for measuring biological information using a wearable electronic device, the method comprising:
    sensing a movement of the electronic device;
    computing a movement value of the electronic device using the sensed movement and detecting a resting state when the movement value is within a predetermined first threshold range during a first time period; and
    configuring biological information of a user wearing the electronic device based on a biological signal for the user measured after detection of the resting state, and
    wherein the first time period is adjusted according to a movement value within a second time period before the first time period.

11. The method of claim 10, further comprising detecting whether the user wears the electronic device.

12. The method of claim 11, further comprising computing the movement value of the electronic device when detecting that the user wears the electronic device.

13. The method of claim 10, wherein configuring the biological information comprises storing one or more additional information related to the biological information in association with the biological information and to display together at least one of the biological information and the additional information.

14. The method of claim 10, wherein when the resting state is detected, activating sensing the biological signal for the user.

15. The method of claim 10, wherein configuring the biological information transfers the configured biological information to another electronic device communicably connected with the electronic device when the biological information is configured.

16. The method of claim 10, wherein whether a movement value within a second time period before the first time period is within a second threshold range larger than the first threshold range is determined when the movement value lasts within the predetermined first threshold range during the first time period, and detecting the resting state when the movement value within the second time period is within the second threshold range.

17. The method of claim 16, wherein the first time period is increased when the movement value within the second time period exceeds the second threshold range.

18. The method of claim 10, wherein control is performed to store the biological information in association with at least one of a date, time, or place of the measurement of the biological signal.

19. A wearable electronic device to be worn on a wrist of a user, comprising:
  a first sensor configured to sense a movement of the electronic device;
  a second sensor configured to sense a biological signal of the user wearing the electronic device; and
  a processor configured to receive, via the first sensor, information relating to the movement of the electronic device, and configure the second sensor to determine a pulse rate of the user based on the biological signal when a movement of the electronic device is less than a predetermined first threshold range during a first time period based on the information received from the first sensor,
  wherein, when a movement of the electronic device is greater than the first threshold range during the first time period, the processor is configured to determine a pulse rate of the user at a later time.

20. The wearable electronic device of claim 19, wherein the electronic device comprises a wrist watch, and the processor is configured to determine whether the wrist watch is currently being worn by a user.

21. The wearable electronic device of claim 19, wherein the processor is configured to activate the second sensor to sense the biological signal if a movement of the electronic device is less than a predetermined first threshold range during a first time period.

22. A method for measuring biological information using a wearable electronic device to be worn on a wrist of a user, the method comprising:
  receiving information relating to a movement of the electronic device;
  determining whether a movement of the electronic device is less than a predetermined first threshold range during a first time period based on the information relating to a movement of the electronic device;
  receiving a biological signal of the user;
  determining a pulse rate of the user based on the biological signal when a movement of the electronic device is less than a predetermined first threshold range during a first time period based on the information relating to a movement of the electronic device; and
  when a movement of the electronic device is greater than the first threshold range during the first time period, determining a pulse rate of the user at a later time.

23. The method of claim 22, wherein the electronic device comprises a wrist watch, and the method further comprising determining whether the wrist watch is currently being worn by a user.

24. The method of claim 22, wherein receiving the biological signal of the user is initiated if a movement of the electronic device is less than a predetermined first threshold range during a first time period.

* * * * *